(12) United States Patent
Ohto et al.

(10) Patent No.: US 9,045,786 B2
(45) Date of Patent: Jun. 2, 2015

(54) GENE THAT INCREASES PRODUCTION OF PLANT FAT-AND-OIL AND METHOD FOR USING THE SAME

(75) Inventors: Chikara Ohto, Toyota (JP); Hiroshi Chatani, Okazaki (JP); Satoshi Kondo, Miyoshi (JP); Norihiro Mitsukawa, Aichi (JP); Nobuhiko Muramoto, Aichi (JP); Masaru Takagi, Ryugasaki (JP); Kyoko Matsui, Tsuchiura (JP)

(73) Assignee: TOYOTA JIDOSHA KABUSHIKI KAISHA, Aichi (JP)

( * ) Notice: Subject to any disclaimer, the term of this patent is extended or adjusted under 35 U.S.C. 154(b) by 833 days.

(21) Appl. No.: 12/921,060

(22) PCT Filed: Mar. 3, 2009

(86) PCT No.: PCT/JP2009/053960
§ 371 (c)(1),
(2), (4) Date: Dec. 6, 2010

(87) PCT Pub. No.: WO2009/110466
PCT Pub. Date: Sep. 11, 2009

(65) Prior Publication Data
US 2011/0081691 A1 Apr. 7, 2011

(30) Foreign Application Priority Data
Mar. 4, 2008 (JP) ................................ 2008-054008

(51) Int. Cl.
C12N 15/82 (2006.01)
C12P 7/64 (2006.01)
C07K 14/415 (2006.01)

(52) U.S. Cl.
CPC ............. *C12P 7/6463* (2013.01); *C07K 14/415* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 5,516,668 A | 5/1996 | Maruta | |
| 5,783,394 A | 7/1998 | Bestwick et al. | |
| 5,914,449 A | 6/1999 | Murase et al. | |
| 6,717,034 B2 | 4/2004 | Jiang | |
| 7,342,148 B2 * | 3/2008 | Takagi et al. | 800/295 |
| 2003/0101481 A1 | 5/2003 | Zhang et al. | |
| 2003/0226173 A1 | 12/2003 | Ratcliffe et al. | |
| 2004/0006797 A1 | 1/2004 | Shi et al. | |
| 2004/0045049 A1 | 3/2004 | Zhang et al. | |
| 2004/0093638 A1 | 5/2004 | Sasaki et al. | |
| 2005/0005333 A1 | 1/2005 | Ruezinsky et al. | |
| 2005/0183169 A1 | 8/2005 | Takagi et al. | |
| 2006/0107345 A1 | 5/2006 | Alexandrov et al. | |
| 2006/0272060 A1 | 11/2006 | Heard et al. | |
| 2007/0022495 A1 | 1/2007 | Reuber et al. | |
| 2008/0072340 A1 | 3/2008 | Troukhan et al. | |
| 2008/0096277 A1 | 4/2008 | Kuroda | |
| 2009/0019605 A1 | 1/2009 | Takagi et al. | |
| 2009/0094717 A1 | 4/2009 | Troukhan et al. | |
| 2009/0116723 A1 | 5/2009 | Okajima et al. | |
| 2009/0178161 A1 | 7/2009 | Arar et al. | |
| 2009/0190821 A1 | 7/2009 | Marugame | |
| 2009/0300790 A1 | 12/2009 | Aharoni et al. | |
| 2010/0311994 A1 | 12/2010 | Chatani et al. | |
| 2011/0010804 A1 | 1/2011 | Chatani et al. | |
| 2011/0099664 A1 | 4/2011 | Takagi et al. | |
| 2011/0209244 A1 | 8/2011 | Takagi et al. | |
| 2012/0144522 A1 | 6/2012 | Kondo et al. | |
| 2012/0159666 A1 | 6/2012 | Yonekura et al. | |
| 2012/0159673 A1 | 6/2012 | Kondo et al. | |

FOREIGN PATENT DOCUMENTS

| | | |
|---|---|---|
| EP | 1469010 A1 | 10/2004 |
| EP | 1586652 A1 | 10/2005 |
| EP | 1702508 A1 | 9/2006 |
| JP | 60-2023 B2 | 1/1985 |
| JP | 02-035358 A | 2/1990 |
| JP | 6-90766 A | 4/1994 |
| JP | 6-217719 A | 8/1994 |
| JP | 6-303925 A | 11/1994 |
| JP | 9-182 A | 1/1997 |
| JP | 9-65840 A | 3/1997 |
| JP | 9-313059 A | 12/1997 |
| JP | 2001-059842 A | 3/2001 |
| JP | 3149951 B2 | 3/2001 |
| JP | 2001-269176 A | 10/2001 |
| JP | 2001-269177 A | 10/2001 |
| JP | 2001-269178 A | 10/2001 |
| JP | 2001-269179 A | 10/2001 |
| JP | 2001-292776 A | 10/2001 |
| JP | 2001-292777 A | 10/2001 |

(Continued)

OTHER PUBLICATIONS

Wahl et al., Meth Enzymol 152:399 (1987).*
Yanhui et al., Plant Mol Biol 60:107-24 (2006).*
Guo et al. PNAS 101-9205 (2004).*
Stracke_Curr Opin Plant Biol_2001.*
Represents_MerriamWebster_2013.*
Dubos_Trends Plant Sci 15-573 (2010).*
Kyoko Matsui, et al., "A Chimeric AtMYB23 Repressor Induces Hairy Roots, Elongation of Leaves and Stems, and Inhibition of the Deposition of Mucilage on Seed Coats in Arabidopsis", Plant Cell Physiology, 2005, pp. 147-155, vol. 46(1), JSPP.
Keiichiro Hiratsu, et al., "Dominant repression of target genes by chimeric repressors that include the EAR motif, a repression domain, in *Arabidopsis*", The Plant Journal, 2003, pp. 733-739, vol. 34, Blackwell Publishing Ltd.

(Continued)

*Primary Examiner* — David H Kruse
*Assistant Examiner* — Russell Boggs
(74) *Attorney, Agent, or Firm* — Sughrue Mion, PLLC

(57) ABSTRACT

This invention is intended to search for a transcription regulator having a novel function of improving the amount of substances produced per individual plant and to enhance such properties in a plant. A chimeric protein resulting from the fusion of a transcription factor belonging a transcription factor family that includes a transcription factor comprising the amino acid sequence as shown in SEQ ID NO: 4 with the repressor domain is expressed in a plant.

2 Claims, 3 Drawing Sheets

(56) References Cited

FOREIGN PATENT DOCUMENTS

| | | |
|---|---|---|
| JP | 3407034 B2 | 10/2001 |
| JP | 3407036 B2 | 10/2001 |
| JP | 3409079 B2 | 10/2001 |
| JP | 2001-333705 A | 12/2001 |
| JP | 3289043 B2 | 6/2002 |
| JP | 2002-524028 A | 8/2002 |
| JP | 3407033 B2 | 3/2003 |
| JP | 3407035 B2 | 3/2003 |
| JP | 3421740 B2 | 4/2003 |
| JP | 2004-500823 A | 1/2004 |
| JP | 2004-286666 A | 10/2004 |
| JP | 2005-013214 A | 1/2005 |
| JP | 2005-027654 A | 2/2005 |
| JP | 2005-052114 A | 3/2005 |
| JP | 3656104 B2 | 6/2005 |
| JP | 2005-192483 A | 7/2005 |
| JP | 2005-204573 A | 8/2005 |
| JP | 2005-204657 A | 8/2005 |
| JP | 2005-278422 A | 10/2005 |
| JP | 2005-295878 A | 10/2005 |
| JP | 2005-295879 A | 10/2005 |
| JP | 2005-325136 A | 11/2005 |
| JP | 2005-352571 A | 12/2005 |
| JP | 2006-006248 A | 1/2006 |
| JP | 2006-020607 A | 1/2006 |
| JP | 2006-034218 A | 2/2006 |
| JP | 2006-042729 A | 2/2006 |
| JP | 2006-042730 A | 2/2006 |
| JP | 2006-055125 A | 3/2006 |
| JP | 2006-101827 A | 4/2006 |
| JP | 2006-134188 A | 5/2006 |
| JP | 3829200 B2 | 7/2006 |
| JP | 2006-280242 A | 10/2006 |
| JP | 2006-325588 A | 12/2006 |
| JP | 3995211 B2 | 10/2007 |
| JP | 2008-502358 A | 1/2008 |
| JP | 2009-009290 A | 1/2009 |
| JP | 2009-115598 A | 5/2009 |
| JP | 2009-180539 A | 8/2009 |
| JP | 2009-210409 A | 9/2009 |
| WO | 00/05385 A1 | 2/2000 |
| WO | 01/35727 A1 | 5/2001 |
| WO | 01/36597 A1 | 5/2001 |
| WO | 01/64022 A2 | 9/2001 |
| WO | WO 03/013227 A2 * | 3/2003 |
| WO | 03/055903 A1 | 7/2003 |
| WO | 2004/031349 A2 | 4/2004 |
| WO | 2004/046336 A2 | 6/2004 |
| WO | 2004/056993 A1 | 7/2004 |
| WO | 2005/047516 A2 | 5/2005 |
| WO | 2005/085467 A1 | 9/2005 |
| WO | 2006/056701 A1 | 6/2006 |
| WO | 2006/133461 A1 | 12/2006 |
| WO | 2007/102346 A1 | 9/2007 |
| WO | 2007/117693 A2 | 10/2007 |
| WO | 2008/041693 A1 | 4/2008 |
| WO | 2010/035618 A1 | 4/2010 |
| WO | 2010/041423 A1 | 4/2010 |

OTHER PUBLICATIONS

Keiichiro Hiratsu, et al., "Identification of the minimal repression domain of SUPERMAN shows that the DLELRL hexapeptide is both necessary and sufficient for repression of transcription in *Arabidopsis*", Biochemical and Biophysical Research Communications, 2004, pp. 172-178, vol. 321, Elsevier Inc.
Keiichiro Hiratsu, et al., "The SUPERMAN protein is an active repressor whose carboxy-terminal repression domain is required for the development of normal flowers", Federation of European Biochemical Societies, 2002, pp. 351-354, vol. 514, Elsevier Science B.V.
Kyoko Matsui, et al., "Suppression of the biosynthesis of proanthocyanidin in *Arabidopsis* by a chimeric PAP1 repressor", Plant Biotechnology Journal, 2004, pp. 487-493, vol. 2, Blackwell Publishing Ltd.
Daniel Zilberman, et al., "ARGONAUTE4 Control of Locus-Specific siRNA Accumulation and DNA and Histone Methylation", Science, Jan. 31, 2003, pp. 716-719, vol. 299.
James P. Jackson, et al., "Control of CpNpG DNA methylation by the KRYPTONITE histone H3 methyltransferase", Nature, Apr. 2, 2002, pp. 556-560, vol. 416, Macmillan Magazines Ltd.
Xiaofeng Cao, et al., "Role of the *Arabidopsis* DRM Methyltransferases in De Novo DNA Methylation and Gene Silencing", Current biology, Jul. 9, 2002, pp. 1138-1144, vol. 12, Elsevier Science Ltd.
Xiaofeng Cao, et al., "Locus-specific control of asymmetric and CpNpG methylation by the DRM and CMT3 methyltransferase genes", PNAS, Dec. 10, 2002, pp. 16491-16498, vol. 99(4).
Lu Tian, et al., "Blocking histone deacetylation in *Arabidopsis* induces pleiotropic effects on plant gene regulation and development", PNAS, Jan. 2, 2001, pp. 200-205, vol. 98(1).
Anders M. Lindroth, et al., Requirement of CHROMOMETHYLASE3 for Maintenance of CpXpG Methylation, Science, Jun. 15, 2001, pp. 2077-2080, vol. 292, the American Association for the Advancement of Science.
Steven E. Jacobsen, et al., "Ectopic hypermethylation of flower-specific genes in *Arabidopsis*", Current Biology, 2000, pp. 179-186, vol. 10, Elsevier Science Ltd.
Steven E. Jacobsen, et al., "Hypermethylated SUPERMAN Epigenetic Alleles in *Arabidopsis*", Science, Aug. 22, 1997, pp. 1100-1103, vol. 277, The American Association for the Advancement of Science.
John L. Bowman, et al., "SUPERMAN, a regulator of floral homeotic genes in *Arabidopsis*", Development, 1992, pp. 599-615, vol. 114, The Company of Biologists Ltd.
J. Christopher Gaiser, et al., "The *Arabidopsis* SUPERMAN Gene Mediates Asymmetric Growth of the Outer Integument of Ovules", The Plant Cell, Mar. 1995, pp. 333-345, vol. 7, American Society of Plant Physiologists.
Koji Goto, et al., "Function and regulation of the *Arabidopsis* floral homeotic gene PISTILLATA", Genes & Development, 1994, pp. 1548-1560, vol. 8, Cold Spring Harbor Laboratory Press.
Keith Roesler, et al., "Targeting of the *Arabidopsis* Homomeric Acetyl-Coenzyme A Carboxylase to Plastids of Rapeseeds", PLant Physiology, 1997, pp. 75-81, vol. 113.
Colette Jako, et al., "Seed-Specific Over-Expression of an *Arabidopsis* cDNA Encoding a Diacylglycerol Acyltransferase Enhances Seed Oil Content and Seed Weight", Plant Physiology, Jun. 2001, pp. 861-874, vol. 126, American Society of Plant Physiologists.
Alex Cernac, et al., "WRINKLED1 encodes an AP2/EREB domain protein involved in the control of storage compound biosynthesis in *Arabidopsis*", 2004, pp. 575-585, vol. 40, Blackwell Publishing Ltd.
Masaru Ohta, et al., "Repression Domains of Class II ERF Transcriptional Repressors Share an Essential Motif for Active Repression", The Plant Cell, Aug. 2001, pp. 1959-1968, vol. 13, American Society of Plant Biologists.
Kyoko Matsui et al., "CRES-T: Chimeric Repressor Silencing Technology", The Bio Medical Quick Review Net 2004, pp. 1-6, vol. 4006.
Shinchiro Sawa, "Overexpression of the AtmybL2 Gene Represses Trichome Development in *Arabidopsis*", DNA Research, 2002, pp. 31-34, vol. 9, No. 2.
Bo Shen et al., "The homeobox gene GLABRA2 affects seed oil content in *Arabidopsis*", Plant Molecular Biology, 2006, pp. 377-387, vol. 60, No. 3 Springer.
Tomotsugu Koyama et al., "TCP Transcription Factors Control the Morphology of Shoot Lateral Organs via Negative Regulation of the Expression of Boundary-Specific Genes in *Arabidopsis* ", The Plant Cell, 2007, 19: 473-484.
Norihto Kuno et al., "The Novel MYB Protein Early-Phytochrome-Responsive1 is a Component of a Slave Circadian Oscillator in *Arabidopsis*", The Plant Cell, 2003, 15: 2476-2488.
Makoto Kusaba et al., "Low glutelin content1: A Dominant Mutation that Suppresses the Glutelin Multigene Family via RNA Silencing in Rice", The Plant Cell, 2003, 15: 1455-1467.

(56) References Cited

OTHER PUBLICATIONS

Nobuhiko Muramoto et al., "Identification of transcription factors responsible for seed oil content by Chimeric Repressor Gene-Silencing Technology (CRES-T)", Suppplemental to Plant and Cell Physiology, 2008, 49: 152.
Diego Mauricio Riano-Pachon et al., "Pln TFDB an intergrative plant transcription factor database", BMC Bioinformatics, 2007, 8(42): 1-10.
Monica Santos-Mendoza et al., "Deciphering gene regulatory networks that control seed development and maturation in *Arabidopsis*", The Plant Jounral, 2008, 54: 608-620.
V.R. Bautista et al., "*Arabidopsis* ORF clones", GenBank Accession BT029518, 2006, retrieved from: http://www.ncbi.nlm.nih.gov/entrez/viewer.fcgi?119360090:NCBI:15965543 on Dec. 25, 2008.
Mingjie Chen et al., "System Analysis of an *Arabidopsis* Mutant Altered in de Novo Fatty Acid Synthesis Reveals Diverse Changes in Seed Composition and Metabolism", Plant Physiology, 2009, 150: 27-41.
Antony N. Dodd et al., "Plant Circadian Clocks Increase Photosynthesis, Growth, Survival, and Competitive Advantage", Science, 2005, 309: 630-633.
John Doebley et al., "The evolution of apical dominance in maize", Nature, 1997, 386: 485-488.
Extended European Search Report (EESR) for corresponding European Patent Application No. 08 85 6425 dated Nov. 3, 2010.
Extended European Search Report (EESR) for corresponding European Patent Application No. 08858128.5 dated Nov. 15, 2010.
Yongfeng Guo et al., "AtNAP, a NAC family transcription factor, has an important role in leaf senescence", The Plant Journal, 2006, 46: 601-612.
Yuxin Hu et al., "The *Arabidopsis* Auxin-Inducible Gene ARGOS Controls Lateral Organ Size", The Plant Cell, 2003, 15: 1951-1961.
Yuxin Hu. et al., "The *Arabidopsis* ARGOS-Like gene regulates cell expansion during organ growth", The Plant Journal, 2006, 47:1-9.
International Search Report for International Application No. PCT/JP2008/072158, dated Feb. 24, 2009.
International Search Report for International Application No. PCT/JP2010/059543, dated Aug. 17, 2010.
K. Diane Jofuku et al., "Control of seed mass and seed yield by the floral homeotic gene APETALA2", PNAS, 2005, 102(8): 3117-3122.
Tomotsugu Koyama et al., "TCP Transcription Factors Control the Morphology of Shoot Lateral Organs via Negative Regulation of the Expression of Boundary-Specific Genes in *Arabidopsis*", The Plant Cell, 2007, 19: 473-484.
Minoru Kubo et al., "Transcription switches for protoxylem and metaxylem vessel formation", Genes & Development, 2005, 19: 1855-1860.
Norihito Kuno et al., "The Novel MYB Protein Early-Phytochrome-Responsive1 is a Component of a Slave Circadian Oscillator in *Arabidopsis*", The Plant Cell, 2003, 15: 2476-2488.
Makoto Kusaba et al., "Low glutelin content1 : A Dominant Mutation that Suppresses the Glutelin Multigene Family via RNA Silencing in Rice", The Plant Cell, 2003, 15: 1455-1467.
Hon-Ming Lam, et al., "Overexpression of the ASN1 Gene Enhances Nitrogen Status in Seeds of *Arabidopsis*", Plant Physiology, 2003, 132: 926-935.
Jisheng Li et al., "Arabidopsis H+ -PPase AVP1 Regulates Auxin-Mediated Organ Development", Science, 2005, 310: 121-125.
Yoshiyuki Maruta et al., "Transgenic rice with reduced glutelin content by transformation with glutelin A antisense gene", Molecular Breeding, 2001, 8:273-284.
Kyoko Matsui et al., "AtMYBL2, a protein with a single MYB domain, acts as a negative regulator of anthocyanin biosynthesis in *Arabidopsis*", The Plant Journal, 2008, 55: 954-967.
Akane Matsushita et al., "AGF1, an AT-Hook Protein, is Necessary for the Negative Feedback of AtGA3ox1 Encoding GA 3-Oxidase", Plant Physiology, 2007, 143: 1152-1162.
Nobutaka Mitsuda et al., "Comprehensive functional analysis of plant-specific NAC transcription factor family using the CRES-T method", Abstracts of the 45th Annual Meeting of the Japanese Society of Plant Physiologists, Mar. 2004, P4-B-16 (813).
Nobutaka Mitsuda et al., "NAC Transcription Factors, NST1 and NST3, Are Key Regulators of the Formation of Secondary Walls in Woody Tissues of *Arabidopsis*", The Plant Cell, 2007, 19: 270-280.
Yukiko Mizukami et al., "Plant organ size control: AINTEGUMENTA regulates growth and cell numbers during organogenesis", PNAS, 2000, 97(2): 942-947.
Nobuhiko Muramoto et al., "Identification of transcription factors responsible for seed oil content by Chimeric Repressor Gene-Silencing Technology (CRES-T)", Supplemental to Plant and Cell Physiology, 2008, 49: 152.
Toshitsugu Nakano et al., "Genome-Wide Analysis of the ERF Gene Family in *Arabidopsis* and Rice", Plant Physiology, 2006, 140: 411-432.
Zhongfu Ni et al., "Altered circadian rhythms regulate growth vigour in hybrids and allopolyploids", Nature, 2009, 457: 327-331.
Ohto, 2011 22nd International Conference on *Arabidopsis* Research, Pub: 501746623.
Akio Ohyama et al., "Environmental risk evaluation of rice plants transformed with chimeric antisense cDNA for glutelin", Breeding Research, 2001, 3: 139-149.
Y. Pan et al., "Molecular Cloning, Expression, Phylogenetic and Functional Characterization of the *Arabidopsis* AP2/EREBP Transcription Factor Family", GenBank Accession AY560877, 2004 retrieved from: http://www.ncbi.nlm.nih.gov/entrez/viewer.fcgi?48479345:NCBI:6713742 on Dec. 25, 2008.
Diego Mauricio Riaño-Pachón et al., "Pln TFDB an integrative plant transcription factor database", BMC Bioinformatics, 2007, 8(42): 1-10.
Monica Santos-Mendoza et al., "Deciphering gene regulatory networks that control seed development and maturation in *Arabidopsis*", The Plant Journal, 2008, 54: 608-620.
Marie C. Schruff et al., "The Auxin Response Factor 2 gene of *Arabidopsis* links auxin signalling, cell division, and the size of seeds and other organs", Development, 2005, 133: 251-261.
S. Takada et al., Genbank Accession No. AB049071, *Arabidopsis thaliana* AtNAC2 mRNA, 2006, 3 pages.
Taito Takeda et al., "RNA interference of the *Arabidopsis* putative transcription factor TCP16 gene results in abortion of early pollen development", Plant Molecular Biology, 2006, 61: 165-177.
Randall J. Weselake et al., "Increasing the flow of carbon into seed oil", Biotechnology Advances, 2009, 27: 866-878.
Joseph A. White et al., "Genomic approaches towards the engineering of oil seeds", Plant Physiology and Biochemistry, 2001, 39: 263-270.
K. Yamada et al., Genbank Accession No. BT005044, *Arabidopsis thaliana* clone U20756 putative jasmonic acid regulatory protein (At3g15510) mRNA, 2003, 3 pages.
James Z. Zhang, "Overexpression Analysis of Plant Transcription Factors", Current Opinion in Plant Biology, 2003, 6: 430-440.
Gaiyun Zhang et al., Phylogeny, gene structures, and expression patterns of the ERF gene family in soybean (*Glycine max* L.), Journal of Experimental Botany, 2008, 59(15): 4095-4107.
Restriction and Election of Species Requirement issued Aug. 16, 2012, in U.S. Appl. No. 12/746,577.
Non-final Office Action issued Feb. 15, 2013 in U.S. Appl. No. 12/746,577.
Election of Species Requirement issued Aug. 16, 2012 in U.S. Appl. No. 12/746,640.
Non-final Office Action issued Nov. 27, 2012 in U.S. Appl. No. 12/746,640.
Final Office Action issued Jul. 2, 2013 in U.S. Appl. No. 12/746,640.
Final Office Action, dated Oct. 23, 2013, issued in U.S. Appl. No. 12/746,577.
Accession No. NM_102146, *Arabidopsis thaliana* AP2 domain-containing transcription factor, putative (AT1G22985) mRNA, complete cds, Database (online), May 2009, retrieved from http://www.ncbi.nlm.nih.gov/nuccore/30688157?sat=13&satkey=2426001 on Feb. 6, 2014.
Summaries of a Conference of Japan Society for Bioscience, Biotechnology and Agrochemistry, 2008, vol. 2008, p. 64.

(56) References Cited

OTHER PUBLICATIONS

Locus: AT2G23760, BEL1-Like Homeodomain 4, BLH4, SAW2, Sawtooth 2, Database (online), Feb. 2013, retrieved from http://www.arabidopsis.org/servlets/TairObject?name=AT2G23760&type=locus on Apr. 4, 2014.

Locus: AT1G43160, RAP2.6, Related to AP2 6, Database (online), Feb. 2013, retrieved from http://www.arabidopsis.org/servlets/TairObject?name=at1g43160&type=locus on Apr. 4, 2014.

Office Action, issued by the United States Patent and Trademark Office on Jan. 2, 2015, in U.S. Appl. No. 13/376,169.

Office Action, issued by the United States Patent and Trademark Office on Feb. 11, 2015, in U.S. Appl. No. 13/376,138.

Office Action, issued by the United States Patent and Trademark Office on Feb. 13, 2015, in U.S. Appl. No. 13/376,326.

Notice of Allowance, issued by the United States Patent and Trademark Office on Feb. 11, 2015, in U.S. Appl. No. 14/222,130.

* cited by examiner

SEQUENCE LISTING

```
<160> NUMBER OF SEQ ID NOS: 29

<210> SEQ ID NO 1
<211> LENGTH: 1026
<212> TYPE: DNA
<213> ORGANISM: Arabidopsis thaliana
<220> FEATURE:
<221> NAME/KEY: CDS
<222> LOCATION: (1)..(1023)

<400> SEQUENCE: 1 atg gat aat tca gct cca gat tcg tta tcc aga tcg gaa acc gcc gtc      48
Met Asp Asn Ser Ala Pro Asp Ser Leu Ser Arg Ser Glu Thr Ala Val
1               5                   10                  15 aca tac gac tca cca tat cca ctc tac gcc atg gct ttc tct tct ctc      96
Thr Tyr Asp Ser Pro Tyr Pro Leu Tyr Ala Met Ala Phe Ser Ser Leu
                20                  25                  30 cgc tca tcc tcc ggt cac aga atc gcc gtc gga agc ttc ctc gaa gat     144
Arg Ser Ser Ser Gly His Arg Ile Ala Val Gly Ser Phe Leu Glu Asp
            35                  40                  45 tac aac aac cgc atc gac att ctc tct ttc gat tcc gat tca atg acc     192
Tyr Asn Asn Arg Ile Asp Ile Leu Ser Phe Asp Ser Asp Ser Met Thr
        50                  55                  60 gtt aag cct ctc ccg aat ctc tcc ttc gag cat cct tat cct cca aca     240
Val Lys Pro Leu Pro Asn Leu Ser Phe Glu His Pro Tyr Pro Pro Thr
65                  70                  75                  80 aag cta atg ttc agt cct cct tct ctc cgt cgt cct tcc tcc gga gat     288
Lys Leu Met Phe Ser Pro Pro Ser Leu Arg Arg Pro Ser Ser Gly Asp
                85                  90                  95 ctc ctc gct tcc tcc ggc gat ttc ctc cgt ctt tgg gaa att aac gaa     336
Leu Leu Ala Ser Ser Gly Asp Phe Leu Arg Leu Trp Glu Ile Asn Glu
            100                 105                 110 gat tca tca acc gtc gag cca atc tcg gtt ctc aac aac agc aaa acg     384
Asp Ser Ser Thr Val Glu Pro Ile Ser Val Leu Asn Asn Ser Lys Thr
        115                 120                 125 agc gag ttt tgt gcg ccg ttg act tcc ttc gat tgg aac gat gta gag     432
Ser Glu Phe Cys Ala Pro Leu Thr Ser Phe Asp Trp Asn Asp Val Glu
    130                 135                 140 ccg aaa cgt ctc gga act tgt agt att gat acg acg tgt acg att tgg     480
Pro Lys Arg Leu Gly Thr Cys Ser Ile Asp Thr Thr Cys Thr Ile Trp
145                 150                 155                 160 gat att gag aag tct gtt gtt gag act cag ctt ata gct cat gat aaa     528
Asp Ile Glu Lys Ser Val Val Glu Thr Gln Leu Ile Ala His Asp Lys
                165                 170                 175 gag gtt cat gac att gct tgg gga gaa gct agg gtt ttc gca tca gtc     576
Glu Val His Asp Ile Ala Trp Gly Glu Ala Arg Val Phe Ala Ser Val
            180                 185                 190 tct gct gat gga tcc gtt agg atc ttt gat tta cgt gat aag gaa cat     624
Ser Ala Asp Gly Ser Val Arg Ile Phe Asp Leu Arg Asp Lys Glu His
        195                 200                 205 tct aca atc att tac gag agt cct cag cct gat acg cct ttg tta aga     672
Ser Thr Ile Ile Tyr Glu Ser Pro Gln Pro Asp Thr Pro Leu Leu Arg
    210                 215                 220 ctt gct tgg aac aaa caa gat ctt aga tat atg gct acg att ttg atg     720
Leu Ala Trp Asn Lys Gln Asp Leu Arg Tyr Met Ala Thr Ile Leu Met
225                 230                 235                 240
```

-continued

```
gat tct aat aag gtt gtg att ctc gat att cgt tcg ccg act atg cct      768
Asp Ser Asn Lys Val Val Ile Leu Asp Ile Arg Ser Pro Thr Met Pro
            245                 250                 255 gtt gct gag ctt gaa aga cat cag gct agt gtg aat gct ata gct tgg      816
Val Ala Glu Leu Glu Arg His Gln Ala Ser Val Asn Ala Ile Ala Trp
        260                 265                 270 gcg cct cag agc tgt aaa cat att tgt tct ggt ggt gat gat aca cag      864
Ala Pro Gln Ser Cys Lys His Ile Cys Ser Gly Gly Asp Asp Thr Gln
    275                 280                 285 gct ctt att tgg gag ctt cct act gtt gct gga ccc aat ggg att gat      912
Ala Leu Ile Trp Glu Leu Pro Thr Val Ala Gly Pro Asn Gly Ile Asp
290                 295                 300 ccg atg tcg gtt tat tcg gct ggt tcg gag att aat cag ttg cag tgg      960
Pro Met Ser Val Tyr Ser Ala Gly Ser Glu Ile Asn Gln Leu Gln Trp
305                 310                 315                 320 tct tct tcg cag cct gat tgg att ggt att gct ttt gct aac aaa atg     1008
Ser Ser Ser Gln Pro Asp Trp Ile Gly Ile Ala Phe Ala Asn Lys Met
                325                 330                 335 cag ctc ctt aga gtt tga                                             1026
Gln Leu Leu Arg Val
            340
```

<210> SEQ ID NO 2
<211> LENGTH: 341
<212> TYPE: PRT
<213> ORGANISM: Arabidopsis thaliana

<400> SEQUENCE: 2

```
Met Asp Asn Ser Ala Pro Asp Ser Leu Ser Arg Ser Glu Thr Ala Val
1               5                   10                  15

Thr Tyr Asp Ser Pro Tyr Pro Leu Tyr Ala Met Ala Phe Ser Ser Leu
            20                  25                  30

Arg Ser Ser Ser Gly His Arg Ile Ala Val Gly Ser Phe Leu Glu Asp
        35                  40                  45

Tyr Asn Asn Arg Ile Asp Ile Leu Ser Phe Asp Ser Asp Ser Met Thr
    50                  55                  60

Val Lys Pro Leu Pro Asn Leu Ser Phe Glu His Pro Tyr Pro Pro Thr
65                  70                  75                  80

Lys Leu Met Phe Ser Pro Pro Ser Leu Arg Arg Pro Ser Ser Gly Asp
                85                  90                  95

Leu Leu Ala Ser Ser Gly Asp Phe Leu Arg Leu Trp Glu Ile Asn Glu
            100                 105                 110

Asp Ser Ser Thr Val Glu Pro Ile Ser Val Leu Asn Ser Lys Thr
        115                 120                 125

Ser Glu Phe Cys Ala Pro Leu Thr Ser Phe Asp Trp Asn Asp Val Glu
    130                 135                 140

Pro Lys Arg Leu Gly Thr Cys Ser Ile Asp Thr Thr Cys Thr Ile Trp
145                 150                 155                 160

Asp Ile Glu Lys Ser Val Val Glu Thr Gln Leu Ile Ala His Asp Lys
                165                 170                 175

Glu Val His Asp Ile Ala Trp Gly Glu Ala Arg Val Phe Ala Ser Val
            180                 185                 190

Ser Ala Asp Gly Ser Val Arg Ile Phe Asp Leu Arg Asp Lys Glu His
        195                 200                 205

Ser Thr Ile Ile Tyr Glu Ser Pro Gln Pro Asp Thr Pro Leu Leu Arg
    210                 215                 220
```

```
Leu Ala Trp Asn Lys Gln Asp Leu Arg Tyr Met Ala Thr Ile Leu Met
225                 230                 235                 240

Asp Ser Asn Lys Val Val Ile Leu Asp Ile Arg Ser Pro Thr Met Pro
            245                 250                 255

Val Ala Glu Leu Glu Arg His Gln Ala Ser Val Asn Ala Ile Ala Trp
        260                 265                 270

Ala Pro Gln Ser Cys Lys His Ile Cys Ser Gly Gly Asp Asp Thr Gln
    275                 280                 285

Ala Leu Ile Trp Glu Leu Pro Thr Val Ala Gly Pro Asn Gly Ile Asp
290                 295                 300

Pro Met Ser Val Tyr Ser Ala Gly Ser Glu Ile Asn Gln Leu Gln Trp
305                 310                 315                 320

Ser Ser Ser Gln Pro Asp Trp Ile Gly Ile Ala Phe Ala Asn Lys Met
            325                 330                 335

Gln Leu Leu Arg Val
            340

<210> SEQ ID NO 3
<211> LENGTH: 588
<212> TYPE: DNA
<213> ORGANISM: Arabidopsis thaliana
<220> FEATURE:
<221> NAME/KEY: CDS
<222> LOCATION: (1)..(585)

<400> SEQUENCE: 3 atg aac aaa acc cgc ctt cgt gct ctc tcc cca cct tcc ggt atg caa    48
Met Asn Lys Thr Arg Leu Arg Ala Leu Ser Pro Pro Ser Gly Met Gln
1               5                   10                  15 cac cgt aag aga tgt cga ttg aga ggt cga aac tac gta agg cca gaa    96
His Arg Lys Arg Cys Arg Leu Arg Gly Arg Asn Tyr Val Arg Pro Glu
                20                  25                  30 gtt aaa caa cgc aac ttc tca aaa gat gaa gac gat ctc atc ctc aag   144
Val Lys Gln Arg Asn Phe Ser Lys Asp Glu Asp Asp Leu Ile Leu Lys
            35                  40                  45 ctt cat gca ctt ctt ggc aat aga tgg tca ttg ata gcg gga aga ttg   192
Leu His Ala Leu Leu Gly Asn Arg Trp Ser Leu Ile Ala Gly Arg Leu
        50                  55                  60 cca gga cga acc gac aac gaa gtt agg atc cat tgg gaa act tac cta   240
Pro Gly Arg Thr Asp Asn Glu Val Arg Ile His Trp Glu Thr Tyr Leu
65                  70                  75                  80 aaa agg aag ctc gta aaa atg gga atc gac cca acc aat cat cgt ctc   288
Lys Arg Lys Leu Val Lys Met Gly Ile Asp Pro Thr Asn His Arg Leu
                85                  90                  95 cac cat cac acc aac tac att tct aga cgt cac ctc cat tct tca cat   336
His His His Thr Asn Tyr Ile Ser Arg Arg His Leu His Ser Ser His
                100                 105                 110 aag gaa cat gaa acc aag att att agt gat caa tct tct tcg gta tcc   384
Lys Glu His Glu Thr Lys Ile Ile Ser Asp Gln Ser Ser Ser Val Ser
        115                 120                 125 gaa tca tgt ggt gta aca att ttg ccc att cca agt acc aat tgc tcg   432
Glu Ser Cys Gly Val Thr Ile Leu Pro Ile Pro Ser Thr Asn Cys Ser
130                 135                 140 gag gat agt act agt acc gga cga agt cat ttg cct gac cta aac att   480
Glu Asp Ser Thr Ser Thr Gly Arg Ser His Leu Pro Asp Leu Asn Ile
145                 150                 155                 160 ggt ctc atc ccg gcc gtg act tct ttg cca gct ctt tgc ctt cag gac   528
Gly Leu Ile Pro Ala Val Thr Ser Leu Pro Ala Leu Cys Leu Gln Asp
                165                 170                 175
```

```
tct agc gaa tcc tct acc aat ggt tca aca ggt caa gaa acg ctt ctt      576
Ser Ser Glu Ser Ser Thr Asn Gly Ser Thr Gly Gln Glu Thr Leu Leu
        180                 185                 190 cta ttc cga tga                                                      588
Leu Phe Arg
        195

<210> SEQ ID NO 4
<211> LENGTH: 195
<212> TYPE: PRT
<213> ORGANISM: Arabidopsis thaliana

<400> SEQUENCE: 4

Met Asn Lys Thr Arg Leu Arg Ala Leu Ser Pro Ser Gly Met Gln
1               5                   10                  15

His Arg Lys Arg Cys Arg Leu Arg Gly Arg Asn Tyr Val Arg Pro Glu
                20                  25                  30

Val Lys Gln Arg Asn Phe Ser Lys Asp Glu Asp Leu Ile Leu Lys
            35                  40                  45

Leu His Ala Leu Leu Gly Asn Arg Trp Ser Leu Ile Ala Gly Arg Leu
        50                  55                  60

Pro Gly Arg Thr Asp Asn Glu Val Arg Ile His Trp Glu Thr Tyr Leu
65                  70                  75                  80

Lys Arg Lys Leu Val Lys Met Gly Ile Asp Pro Thr Asn His Arg Leu
                85                  90                  95

His His Thr Asn Tyr Ile Ser Arg Arg His Leu His Ser Ser His
            100                 105                 110

Lys Glu His Glu Thr Lys Ile Ile Ser Asp Gln Ser Ser Val Ser
        115                 120                 125

Glu Ser Cys Gly Val Thr Ile Leu Pro Ile Pro Ser Thr Asn Cys Ser
130                 135                 140

Glu Asp Ser Thr Ser Thr Gly Arg Ser His Leu Pro Asp Leu Asn Ile
145                 150                 155                 160

Gly Leu Ile Pro Ala Val Thr Ser Leu Pro Ala Leu Cys Leu Gln Asp
                165                 170                 175

Ser Ser Glu Ser Ser Thr Asn Gly Ser Thr Gly Gln Thr Leu Leu
        180                 185                 190

Leu Phe Arg
        195

<210> SEQ ID NO 5
<211> LENGTH: 1188
<212> TYPE: DNA
<213> ORGANISM: Arabidopsis thaliana
<220> FEATURE:
<221> NAME/KEY: CDS
<222> LOCATION: (1)..(1185)

<400> SEQUENCE: 5 atg gtg atg gct ggt gct tct tct ttg gat gag atc aga cag gct cag      48
Met Val Met Ala Gly Ala Ser Ser Leu Asp Glu Ile Arg Gln Ala Gln
1               5                   10                  15 aga gct gat gga cct gca ggc atc ttg gct att ggc act gct aac cct      96
Arg Ala Asp Gly Pro Ala Gly Ile Leu Ala Ile Gly Thr Ala Asn Pro
                20                  25                  30 gag aac cat gtg ctt cag gcg gag tat cct gac tac tac ttc cgc atc     144
Glu Asn His Val Leu Gln Ala Glu Tyr Pro Asp Tyr Tyr Phe Arg Ile
            35                  40                  45 acc aac agt gaa cac atg acc gac ctc aag gag aag ttc aag cgc atg     192
```

```
                    Thr Asn Ser Glu His Met Thr Asp Leu Lys Glu Lys Phe Lys Arg Met
                        50                  55                  60 tgc gac aag tcg aca att cgg aaa cgt cac atg cat ctg acg gag gaa         240
Cys Asp Lys Ser Thr Ile Arg Lys Arg His Met His Leu Thr Glu Glu
65                  70                  75                  80 ttc ctc aag gaa aac cca cac atg tgt gct tac atg gct cct tct ctg         288
Phe Leu Lys Glu Asn Pro His Met Cys Ala Tyr Met Ala Pro Ser Leu
                85                  90                  95 gac acc aga cag gac atc gtg gtg gtc gaa gtc cct aag cta ggc aaa         336
Asp Thr Arg Gln Asp Ile Val Val Val Glu Val Pro Lys Leu Gly Lys
            100                 105                 110 gaa gcg gca gtg aag gcc atc aag gag tgg ggc cag ccc aag tca aag         384
Glu Ala Ala Val Lys Ala Ile Lys Glu Trp Gly Gln Pro Lys Ser Lys
        115                 120                 125 atc act cat gtc gtc ttc tgc act acc tcc ggc gtc gac atg cct ggt         432
Ile Thr His Val Val Phe Cys Thr Thr Ser Gly Val Asp Met Pro Gly
    130                 135                 140 gct gac tac cag ctc acc aag ctt ctt ggt ctc cgt cct tcc gtc aag         480
Ala Asp Tyr Gln Leu Thr Lys Leu Leu Gly Leu Arg Pro Ser Val Lys
145                 150                 155                 160 cgt ctc atg atg tac cag caa ggt tgc ttc gcc ggc ggt act gtc ctc         528
Arg Leu Met Met Tyr Gln Gln Gly Cys Phe Ala Gly Gly Thr Val Leu
                165                 170                 175 cgt atc gct aag gat ctc gcc gag aac aat cgt gga gca cgt gtc ctc         576
Arg Ile Ala Lys Asp Leu Ala Glu Asn Asn Arg Gly Ala Arg Val Leu
            180                 185                 190 gtt gtc tgc tct gag atc aca gcc gtt acc ttc cgt ggt ccc tct gac         624
Val Val Cys Ser Glu Ile Thr Ala Val Thr Phe Arg Gly Pro Ser Asp
        195                 200                 205 acc cac ctt gac tcc ctc gtc ggt cag gct ctt ttc agt gat ggc gcc         672
Thr His Leu Asp Ser Leu Val Gly Gln Ala Leu Phe Ser Asp Gly Ala
    210                 215                 220 gcc gca ctc att gtg ggg tcg gac cct gac aca tct gtc gga gag aaa         720
Ala Ala Leu Ile Val Gly Ser Asp Pro Asp Thr Ser Val Gly Glu Lys
225                 230                 235                 240 ccc atc ttt gag atg gtg tct gcc gct cag acc atc ctt cca gac tct         768
Pro Ile Phe Glu Met Val Ser Ala Ala Gln Thr Ile Leu Pro Asp Ser
                245                 250                 255 gat ggt gcc ata gac gga cat ttg agg gaa gtt ggt ctc acc ttc cat         816
Asp Gly Ala Ile Asp Gly His Leu Arg Glu Val Gly Leu Thr Phe His
            260                 265                 270 ctc ctc aag gat gtt ccc ggc ctc atc tcc aag aac att gtg aag agt         864
Leu Leu Lys Asp Val Pro Gly Leu Ile Ser Lys Asn Ile Val Lys Ser
        275                 280                 285 cta gac gaa gcg ttt aaa cct ttg ggg ata agt gac tgg aac tcc ctc         912
Leu Asp Glu Ala Phe Lys Pro Leu Gly Ile Ser Asp Trp Asn Ser Leu
    290                 295                 300 ttc tgg ata gcc cac cct gga ggt cca gcg atc cta gac cag gtg gag         960
Phe Trp Ile Ala His Pro Gly Gly Pro Ala Ile Leu Asp Gln Val Glu
305                 310                 315                 320 ata aag cta gga cta aag gaa gag aag atg agg gcg aca cgt cac gtg         1008
Ile Lys Leu Gly Leu Lys Glu Glu Lys Met Arg Ala Thr Arg His Val
                325                 330                 335 ttg agc gag tat gga aac atg tcg agc gcg tgc gtt ctc ttc ata cta         1056
Leu Ser Glu Tyr Gly Asn Met Ser Ser Ala Cys Val Leu Phe Ile Leu
            340                 345                 350 gac gag atg agg agg aag tca gct aag gat ggt gtg gcc acg aca gga         1104
Asp Glu Met Arg Arg Lys Ser Ala Lys Asp Gly Val Ala Thr Thr Gly
        355                 360                 365
```

```
gaa ggg ttg gag tgg ggt gtc ttg ttt ggt ttc gga cca ggt ctc act    1152
Glu Gly Leu Glu Trp Gly Val Leu Phe Gly Phe Gly Pro Gly Leu Thr
370                 375                 380 gtt gag aca gtc gtc ttg cac agc gtt cct ctc taa                    1188
Val Glu Thr Val Val Leu His Ser Val Pro Leu
385                 390                 395
```

<210> SEQ ID NO 6
<211> LENGTH: 395
<212> TYPE: PRT
<213> ORGANISM: Arabidopsis thaliana

<400> SEQUENCE: 6

```
Met Val Met Ala Gly Ala Ser Ser Leu Asp Glu Ile Arg Gln Ala Gln
1               5                   10                  15

Arg Ala Asp Gly Pro Ala Gly Ile Leu Ala Ile Gly Thr Ala Asn Pro
            20                  25                  30

Glu Asn His Val Leu Gln Ala Glu Tyr Pro Asp Tyr Tyr Phe Arg Ile
        35                  40                  45

Thr Asn Ser Glu His Met Thr Asp Leu Lys Glu Lys Phe Lys Arg Met
    50                  55                  60

Cys Asp Lys Ser Thr Ile Arg Lys Arg His Met His Leu Thr Glu Glu
65                  70                  75                  80

Phe Leu Lys Glu Asn Pro His Met Cys Ala Tyr Met Ala Pro Ser Leu
                85                  90                  95

Asp Thr Arg Gln Asp Ile Val Val Glu Val Pro Lys Leu Gly Lys
            100                 105                 110

Glu Ala Ala Val Lys Ala Ile Lys Glu Trp Gly Gln Pro Lys Ser Lys
        115                 120                 125

Ile Thr His Val Val Phe Cys Thr Thr Ser Gly Val Asp Met Pro Gly
    130                 135                 140

Ala Asp Tyr Gln Leu Thr Lys Leu Leu Gly Leu Arg Pro Ser Val Lys
145                 150                 155                 160

Arg Leu Met Met Tyr Gln Gln Gly Cys Phe Ala Gly Gly Thr Val Leu
                165                 170                 175

Arg Ile Ala Lys Asp Leu Ala Glu Asn Asn Arg Gly Ala Arg Val Leu
            180                 185                 190

Val Val Cys Ser Glu Ile Thr Ala Val Thr Phe Arg Gly Pro Ser Asp
        195                 200                 205

Thr His Leu Asp Ser Leu Val Gly Gln Ala Leu Phe Ser Asp Gly Ala
    210                 215                 220

Ala Ala Leu Ile Val Gly Ser Asp Pro Asp Thr Ser Val Gly Glu Lys
225                 230                 235                 240

Pro Ile Phe Glu Met Val Ser Ala Ala Gln Thr Ile Leu Pro Asp Ser
                245                 250                 255

Asp Gly Ala Ile Asp Gly His Leu Arg Glu Val Gly Leu Thr Phe His
            260                 265                 270

Leu Leu Lys Asp Val Pro Gly Leu Ile Ser Lys Asn Ile Val Lys Ser
        275                 280                 285

Leu Asp Glu Ala Phe Lys Pro Leu Gly Ile Ser Asp Trp Asn Ser Leu
    290                 295                 300

Phe Trp Ile Ala His Pro Gly Gly Pro Ala Ile Leu Asp Gln Val Glu
305                 310                 315                 320

Ile Lys Leu Gly Leu Lys Glu Glu Lys Met Arg Ala Thr Arg His Val
                325                 330                 335
```

```
Leu Ser Glu Tyr Gly Asn Met Ser Ser Ala Cys Val Leu Phe Ile Leu
            340                 345                 350

Asp Glu Met Arg Arg Lys Ser Ala Lys Asp Gly Val Ala Thr Thr Gly
        355                 360                 365

Glu Gly Leu Glu Trp Gly Val Leu Phe Gly Phe Gly Pro Gly Leu Thr
    370                 375                 380

Val Glu Thr Val Val Leu His Ser Val Pro Leu
385                 390                 395

<210> SEQ ID NO 7
<211> LENGTH: 741
<212> TYPE: DNA
<213> ORGANISM: Arabidopsis thaliana
<220> FEATURE:
<221> NAME/KEY: CDS
<222> LOCATION: (1)..(738)

<400> SEQUENCE: 7 atg tct tca tcc aac gcc tgc gcc tct ccg tca ccg ttc ccc gcc gtc    48
Met Ser Ser Ser Asn Ala Cys Ala Ser Pro Ser Pro Phe Pro Ala Val
1               5                   10                  15 acg aag ctt cat gta gac tcc gtc acg ttt gta ccg tcc gtc aag tca    96
Thr Lys Leu His Val Asp Ser Val Thr Phe Val Pro Ser Val Lys Ser
            20                  25                  30 ccg gcc tcc tcc aat cca tta ttc ctc ggc ggc gcc ggt gtc cga ggc   144
Pro Ala Ser Ser Asn Pro Leu Phe Leu Gly Gly Ala Gly Val Arg Gly
        35                  40                  45 ctt gat atc caa ggt aaa ttc gtg atc ttc acc gtc att gga gta tac   192
Leu Asp Ile Gln Gly Lys Phe Val Ile Phe Thr Val Ile Gly Val Tyr
    50                  55                  60 cta gag ggt aac gcc gtt cct tct cta tct gtc aag tgg aag gga aaa   240
Leu Glu Gly Asn Ala Val Pro Ser Leu Ser Val Lys Trp Lys Gly Lys
65                  70                  75                  80 act acg gag gag cta aca gaa tct atc ccg ttc ttc cgt gaa ata gtc   288
Thr Thr Glu Glu Leu Thr Glu Ser Ile Pro Phe Phe Arg Glu Ile Val
                85                  90                  95 acc ggt gcg ttt gag aag ttt atc aag gtg aca atg aaa ctg ccg tta   336
Thr Gly Ala Phe Glu Lys Phe Ile Lys Val Thr Met Lys Leu Pro Leu
            100                 105                 110 acg gga caa caa tat tcg gag aaa gtg acg gag aat tgt gtg gct ata   384
Thr Gly Gln Gln Tyr Ser Glu Lys Val Thr Glu Asn Cys Val Ala Ile
        115                 120                 125 tgg aaa caa tta ggg ctt tat acg gac tgt gaa gct aaa gct gtg gag   432
Trp Lys Gln Leu Gly Leu Tyr Thr Asp Cys Glu Ala Lys Ala Val Glu
    130                 135                 140 aag ttc ttg gag atc ttc aag gaa gaa aca ttc cct ccc ggt tca tcg   480
Lys Phe Leu Glu Ile Phe Lys Glu Glu Thr Phe Pro Pro Gly Ser Ser
145                 150                 155                 160 atc ctc ttc gct ctc tcc cct acc ggc tct ctt acg gtt gcg ttt tcg   528
Ile Leu Phe Ala Leu Ser Pro Thr Gly Ser Leu Thr Val Ala Phe Ser
                165                 170                 175 aaa gat gat agt atc cct gaa acc ggg atc gct gtg atc gag aac aaa   576
Lys Asp Asp Ser Ile Pro Glu Thr Gly Ile Ala Val Ile Glu Asn Lys
            180                 185                 190 ttg ttg gcg gag gcg gtt ctg gaa tct atc atc ggg aag aac ggt gtg   624
Leu Leu Ala Glu Ala Val Leu Glu Ser Ile Ile Gly Lys Asn Gly Val
        195                 200                 205 tca cct ggc act agg tta agt gtt gca gaa aga tta tct cag cta atg   672
Ser Pro Gly Thr Arg Leu Ser Val Ala Glu Arg Leu Ser Gln Leu Met
    210                 215                 220
```

```
atg aag aac aag gac gaa aag gaa gtt agt gat cac tct gtt gag gaa    720
Met Lys Asn Lys Asp Glu Lys Glu Val Ser Asp His Ser Val Glu Glu
225                 230                 235                 240 aaa cta gcc aaa gag aac tga                                        741
Lys Leu Ala Lys Glu Asn
                245
```

<210> SEQ ID NO 8
<211> LENGTH: 246
<212> TYPE: PRT
<213> ORGANISM: Arabidopsis thaliana

<400> SEQUENCE: 8

```
Met Ser Ser Asn Ala Cys Ala Ser Pro Ser Pro Phe Pro Ala Val
1               5                   10                  15

Thr Lys Leu His Val Asp Ser Val Thr Phe Val Pro Ser Val Lys Ser
                20                  25                  30

Pro Ala Ser Ser Asn Pro Leu Phe Leu Gly Gly Ala Gly Val Arg Gly
            35                  40                  45

Leu Asp Ile Gln Gly Lys Phe Val Ile Phe Thr Val Ile Gly Val Tyr
 50                  55                  60

Leu Glu Gly Asn Ala Val Pro Ser Leu Ser Val Lys Trp Lys Gly Lys
65                  70                  75                  80

Thr Thr Glu Glu Leu Thr Glu Ser Ile Pro Phe Phe Arg Glu Ile Val
                    85                  90                  95

Thr Gly Ala Phe Glu Lys Phe Ile Lys Val Thr Met Lys Leu Pro Leu
                100                 105                 110

Thr Gly Gln Gln Tyr Ser Glu Lys Val Thr Glu Asn Cys Val Ala Ile
            115                 120                 125

Trp Lys Gln Leu Gly Leu Tyr Thr Asp Cys Glu Ala Lys Ala Val Glu
130                 135                 140

Lys Phe Leu Glu Ile Phe Lys Glu Glu Thr Phe Pro Pro Gly Ser Ser
145                 150                 155                 160

Ile Leu Phe Ala Leu Ser Pro Thr Gly Ser Leu Thr Val Ala Phe Ser
                165                 170                 175

Lys Asp Asp Ser Ile Pro Glu Thr Gly Ile Ala Val Ile Glu Asn Lys
            180                 185                 190

Leu Leu Ala Glu Ala Val Leu Glu Ser Ile Ile Gly Lys Asn Gly Val
        195                 200                 205

Ser Pro Gly Thr Arg Leu Ser Val Ala Glu Arg Leu Ser Gln Leu Met
    210                 215                 220

Met Lys Asn Lys Asp Glu Lys Glu Val Ser Asp His Ser Val Glu Glu
225                 230                 235                 240

Lys Leu Ala Lys Glu Asn
                245
```

<210> SEQ ID NO 9
<211> LENGTH: 1077
<212> TYPE: DNA
<213> ORGANISM: Arabidopsis thaliana
<220> FEATURE:
<221> NAME/KEY: CDS
<222> LOCATION: (1)..(1074)

<400> SEQUENCE: 9

```
atg gct cca gga act ttg act gag cta gcc gga gag tct aag ctc aac    48
Met Ala Pro Gly Thr Leu Thr Glu Leu Ala Gly Glu Ser Lys Leu Asn
1               5                   10                  15
```

-continued

| | | |
|---|---|---|
| tct aaa ttt gtc agg gac gaa gat gaa cgg ccc aaa gtc gct tac aat<br>Ser Lys Phe Val Arg Asp Glu Asp Glu Arg Pro Lys Val Ala Tyr Asn<br>20                      25                    30 | 96 |
| gtg ttt agc gac gaa atc ccg gtg atc tct ctc gcc ggt atc gat gac<br>Val Phe Ser Asp Glu Ile Pro Val Ile Ser Leu Ala Gly Ile Asp Asp<br>          35                    40                    45 | 144 |
| gtc gat gga aaa aga gga gag atc tgc cgt cag atc gtt gag gct tgt<br>Val Asp Gly Lys Arg Gly Glu Ile Cys Arg Gln Ile Val Glu Ala Cys<br>50                      55                    60 | 192 |
| gag aat tgg ggc atc ttc caa gtg gtc gat cac ggc gtc gat act aac<br>Glu Asn Trp Gly Ile Phe Gln Val Val Asp His Gly Val Asp Thr Asn<br>65                      70                    75                    80 | 240 |
| tta gtg gcg gat atg act cgt ctc gct cgt gac ttc ttt gct tta cct<br>Leu Val Ala Asp Met Thr Arg Leu Ala Arg Asp Phe Phe Ala Leu Pro<br>                    85                    90                    95 | 288 |
| ccg gaa gac aag ctc cgt ttc gac atg tcc ggt ggt aaa aaa gga gga<br>Pro Glu Asp Lys Leu Arg Phe Asp Met Ser Gly Gly Lys Lys Gly Gly<br>100                      105                    110 | 336 |
| ttc atc gtc tct agt cac ctc cag gga gag gct gtg caa gat tgg aga<br>Phe Ile Val Ser Ser His Leu Gln Gly Glu Ala Val Gln Asp Trp Arg<br>                115                    120                    125 | 384 |
| gag att gta acg tat ttc tcg tac ccg gtg aga aac aga gac tac tca<br>Glu Ile Val Thr Tyr Phe Ser Tyr Pro Val Arg Asn Arg Asp Tyr Ser<br>130                      135                    140 | 432 |
| cgg tgg cca gat aag ccg gaa ggt tgg gtg aaa gtg acg gag gag tat<br>Arg Trp Pro Asp Lys Pro Glu Gly Trp Val Lys Val Thr Glu Glu Tyr<br>145                      150                    155                    160 | 480 |
| agt gag agg ctt atg agt ttg gct tgt aag ctt ctt gag gtt ttg tct<br>Ser Glu Arg Leu Met Ser Leu Ala Cys Lys Leu Leu Glu Val Leu Ser<br>                      165                    170                    175 | 528 |
| gaa gct atg ggt ctt gag aaa gag tct ctt acc aat gca tgc gtc gat<br>Glu Ala Met Gly Leu Glu Lys Glu Ser Leu Thr Asn Ala Cys Val Asp<br>180                      185                    190 | 576 |
| atg gac caa aag att gtt gtt aat tat tac cca aaa tgc cct cag cct<br>Met Asp Gln Lys Ile Val Val Asn Tyr Tyr Pro Lys Cys Pro Gln Pro<br>                195                    200                    205 | 624 |
| gat ctc acc ctc gga ctc aag cgt cac act gac cct gga acc att acc<br>Asp Leu Thr Leu Gly Leu Lys Arg His Thr Asp Pro Gly Thr Ile Thr<br>210                      215                    220 | 672 |
| ttg ctg cta caa gac caa gtc ggt gga tta caa gcc aca cgt gac aat<br>Leu Leu Leu Gln Asp Gln Val Gly Gly Leu Gln Ala Thr Arg Asp Asn<br>225                      230                    235                    240 | 720 |
| ggc aag aca tgg att acg gtt cag cct gtt gaa gga gcg ttt gtc gtc<br>Gly Lys Thr Trp Ile Thr Val Gln Pro Val Glu Gly Ala Phe Val Val<br>                      245                    250                    255 | 768 |
| aat ctc ggc gac cac ggc cat ttt ttg agc aat ggg agg ttc aag aat<br>Asn Leu Gly Asp His Gly His Phe Leu Ser Asn Gly Arg Phe Lys Asn<br>260                      265                    270 | 816 |
| gct gat cat cag gcc gtg gtg aac tct aac tcg agc aga tta tcc ata<br>Ala Asp His Gln Ala Val Val Asn Ser Asn Ser Ser Arg Leu Ser Ile<br>                275                    280                    285 | 864 |
| gcc acg ttc cag aac ccc gcg ccg gat gcc aca gtg tat cca ctg aaa<br>Ala Thr Phe Gln Asn Pro Ala Pro Asp Ala Thr Val Tyr Pro Leu Lys<br>290                      295                    300 | 912 |
| gta aga gaa gga gag aag gca ata ttg gag gag cca atc acg ttt gcc<br>Val Arg Glu Gly Glu Lys Ala Ile Leu Glu Glu Pro Ile Thr Phe Ala<br>305                      310                    315                    320 | 960 |
| gag atg tat aag aga aag atg gga aga gat ttg gag ctt gct cgc ctc<br>Glu Met Tyr Lys Arg Lys Met Gly Arg Asp Leu Glu Leu Ala Arg Leu<br>                      325                    330                    335 | 1008 |

```
aag aag ctg gct aaa gag gag cgt gac cac aaa gaa gtt gac aag cct    1056
Lys Lys Leu Ala Lys Glu Glu Arg Asp His Lys Glu Val Asp Lys Pro
        340                 345                 350 gtc gac caa atc ttc gct tag                                        1077
Val Asp Gln Ile Phe Ala
        355
```

<210> SEQ ID NO 10
<211> LENGTH: 358
<212> TYPE: PRT
<213> ORGANISM: Arabidopsis thaliana

<400> SEQUENCE: 10

```
Met Ala Pro Gly Thr Leu Thr Glu Leu Ala Gly Ser Lys Leu Asn
1               5                   10                  15

Ser Lys Phe Val Arg Asp Glu Asp Arg Pro Lys Val Ala Tyr Asn
                20                  25                  30

Val Phe Ser Asp Glu Ile Pro Val Ile Ser Leu Ala Gly Ile Asp Asp
                35                  40                  45

Val Asp Gly Lys Arg Gly Glu Ile Cys Arg Gln Ile Val Glu Ala Cys
50                  55                  60

Glu Asn Trp Gly Ile Phe Gln Val Val Asp His Gly Val Asp Thr Asn
65                  70                  75                  80

Leu Val Ala Asp Met Thr Arg Leu Ala Arg Asp Phe Phe Ala Leu Pro
                85                  90                  95

Pro Glu Asp Lys Leu Arg Phe Asp Met Ser Gly Gly Lys Lys Gly Gly
                100                 105                 110

Phe Ile Val Ser Ser His Leu Gln Gly Glu Ala Val Gln Asp Trp Arg
                115                 120                 125

Glu Ile Val Thr Tyr Phe Ser Tyr Pro Val Arg Asn Arg Asp Tyr Ser
                130                 135                 140

Arg Trp Pro Asp Lys Pro Glu Gly Trp Val Lys Val Thr Glu Glu Tyr
145                 150                 155                 160

Ser Glu Arg Leu Met Ser Leu Ala Cys Lys Leu Leu Glu Val Leu Ser
                165                 170                 175

Glu Ala Met Gly Leu Glu Lys Glu Ser Leu Thr Asn Ala Cys Val Asp
                180                 185                 190

Met Asp Gln Lys Ile Val Asn Tyr Tyr Pro Lys Cys Pro Gln Pro
                195                 200                 205

Asp Leu Thr Leu Gly Leu Lys Arg His Thr Asp Pro Gly Thr Ile Thr
    210                 215                 220

Leu Leu Leu Gln Asp Gln Val Gly Gly Leu Gln Ala Thr Arg Asp Asn
225                 230                 235                 240

Gly Lys Thr Trp Ile Thr Val Gln Pro Val Glu Gly Ala Phe Val Val
                245                 250                 255

Asn Leu Gly Asp His Gly His Phe Leu Ser Asn Gly Arg Phe Lys Asn
                260                 265                 270

Ala Asp His Gln Ala Val Val Asn Ser Asn Ser Ser Arg Leu Ser Ile
    275                 280                 285

Ala Thr Phe Gln Asn Pro Ala Pro Asp Ala Thr Val Tyr Pro Leu Lys
                290                 295                 300

Val Arg Glu Gly Glu Lys Ala Ile Leu Glu Glu Pro Ile Thr Phe Ala
305                 310                 315                 320

Glu Met Tyr Lys Arg Lys Met Gly Arg Asp Leu Glu Leu Ala Arg Leu
                325                 330                 335
```

-continued

Lys Lys Leu Ala Lys Glu Glu Arg Asp His Lys Glu Val Asp Lys Pro
        340                 345                 350

Val Asp Gln Ile Phe Ala
        355

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      forward primer 1 of At1g71030

<400> SEQUENCE: 11
gatgaacaaa acccgccttc gtgctctctc                                    30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      reverse primer 1 of At1g71030

<400> SEQUENCE: 12
tcggaataga agaagcgttt cttgacctgt                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      forward primer 2 of At1g71030

<400> SEQUENCE: 13
gatgaacaaa acccgccttc gtgctctctc                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      reverse primer 2 of At1g71030

<400> SEQUENCE: 14
tcatcggaat agaagaagcg tttcttgacc                                    30

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      forward primer of At1g56650

<400> SEQUENCE: 15
gatggagggt tcgtccaaag ggc                                           23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic reverse primer of At1g56650

<400> SEQUENCE: 16
atcaaatttc acagtctctc catcg                                    25

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      forward primer of At5g24520

<400> SEQUENCE: 17
gatggataat tcagctccag attcgttatc                               30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      reverse primer of At5g24520

<400> SEQUENCE: 18
aactctaagg agctgcattt tgttagcaaa                               30

<210> SEQ ID NO 19
<211> LENGTH: 747
<212> TYPE: DNA
<213> ORGANISM: Arabidopsis thaliana
<220> FEATURE:
<221> NAME/KEY: CDS
<222> LOCATION: (1)..(744)

<400> SEQUENCE: 19

```
atg gag ggt tcg tcc aaa ggg ctg cga aaa ggt gct tgg act act gaa      48
Met Glu Gly Ser Ser Lys Gly Leu Arg Lys Gly Ala Trp Thr Thr Glu
 1               5                  10                  15 gaa gat agt ctc ttg aga cag tgc att aat aag tat gga gaa ggc aaa      96
Glu Asp Ser Leu Leu Arg Gln Cys Ile Asn Lys Tyr Gly Glu Gly Lys
             20                  25                  30 tgg cac caa gtt cct gta aga gct ggg cta aac cgg tgc agg aaa agt     144
Trp His Gln Val Pro Val Arg Ala Gly Leu Asn Arg Cys Arg Lys Ser
         35                  40                  45 tgt aga tta aga tgg ttg aac tat ttg aag cca agt atc aag aga gga     192
Cys Arg Leu Arg Trp Leu Asn Tyr Leu Lys Pro Ser Ile Lys Arg Gly
     50                  55                  60 aaa ctt agc tct gat gaa gtc gat ctt ctt ctt cgc ctt cat agg ctt     240
Lys Leu Ser Ser Asp Glu Val Asp Leu Leu Leu Arg Leu His Arg Leu
 65                  70                  75                  80 cta ggg aat agg tgg tct tta att gct gga aga tta cct ggt cgg acc     288
Leu Gly Asn Arg Trp Ser Leu Ile Ala Gly Arg Leu Pro Gly Arg Thr
                 85                  90                  95 gca aat gac gtc aag aat tac tgg aac act cat ctg agt aag aaa cat     336
Ala Asn Asp Val Lys Asn Tyr Trp Asn Thr His Leu Ser Lys Lys His
            100                 105                 110 gaa ccg tgt tgt aag ata aag atg aaa aag aga gac att acg ccc att     384
Glu Pro Cys Cys Lys Ile Lys Met Lys Lys Arg Asp Ile Thr Pro Ile
        115                 120                 125 cct aca aca ccg gca cta aaa aac aat gtt tat aag cct cga cct cga     432
Pro Thr Thr Pro Ala Leu Lys Asn Asn Val Tyr Lys Pro Arg Pro Arg
    130                 135                 140
```

```
tcc ttc aca gtt aac aac gac tgc aac cat ctc aat gcc cca cca aaa      480
Ser Phe Thr Val Asn Asn Asp Cys Asn His Leu Asn Ala Pro Pro Lys
145                 150                 155                 160 gtt gac gtt aat cct cca tgc ctt gga ctt aac atc aat aat gtt tgt      528
Val Asp Val Asn Pro Pro Cys Leu Gly Leu Asn Ile Asn Asn Val Cys
                165                 170                 175 gac aat agt atc ata tac aac aaa gat aag aag aaa gac caa cta gtg      576
Asp Asn Ser Ile Ile Tyr Asn Lys Asp Lys Lys Lys Asp Gln Leu Val
            180                 185                 190 aat aat ttg att gat gga gat aat atg tgg tta gag aaa ttc cta gag      624
Asn Asn Leu Ile Asp Gly Asp Asn Met Trp Leu Glu Lys Phe Leu Glu
        195                 200                 205 gaa agc caa gag gta gat att ttg gtt cct gaa gcg acg aca aca gaa      672
Glu Ser Gln Glu Val Asp Ile Leu Val Pro Glu Ala Thr Thr Thr Glu
    210                 215                 220 aag ggg gac acc ttg gct ttt gac gtt gat caa ctt tgg agt ctt ttc      720
Lys Gly Asp Thr Leu Ala Phe Asp Val Asp Gln Leu Trp Ser Leu Phe
225                 230                 235                 240 gat gga gag act gtg aaa ttt gat tag                                  747
Asp Gly Glu Thr Val Lys Phe Asp
                245
```

<210> SEQ ID NO 20
<211> LENGTH: 248
<212> TYPE: PRT
<213> ORGANISM: Arabidopsis thaliana

<400> SEQUENCE: 20

```
Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
```

```
                    225                 230                 235                 240

Asp Gly Glu Thr Val Lys Phe Asp
                245

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Any amino acid and this region may encompass
      0 to 10 residues
<220> FEATURE:
<221> NAME/KEY: MOD_RES
<222> LOCATION: (14)..(14)
<223> OTHER INFORMATION: Asn or Glu
<220> FEATURE:
<221> NAME/KEY: MOD_RES
<222> LOCATION: (16)..(21)
<223> OTHER INFORMATION: Any amino acid
<220> FEATURE:
<223> OTHER INFORMATION: See specification as filed for detailed
      description of substitutions and preferred embodiments

<400> SEQUENCE: 21

Xaa Xaa Xaa Xaa Xaa Xaa Xaa Xaa Xaa Xaa Leu Asp Leu Xaa Leu Xaa
1               5                   10                  15

Xaa Xaa Xaa Xaa Xaa
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Any amino acid and this region may encompass 0
      to 10 residues
<220> FEATURE:
<221> NAME/KEY: MOD_RES
<222> LOCATION: (15)..(15)
<223> OTHER INFORMATION: Phe or Ile
<220> FEATURE:
<221> NAME/KEY: MOD_RES
<222> LOCATION: (16)..(21)
<223> OTHER INFORMATION: Any amino acid
<220> FEATURE:
<223> OTHER INFORMATION: See specification as filed for detailed
      description of substitutions and preferred embodiments

<400> SEQUENCE: 22

Xaa Xaa Xaa Xaa Xaa Xaa Xaa Xaa Xaa Xaa Phe Asp Leu Asn Xaa Xaa
1               5                   10                  15

Xaa Xaa Xaa Xaa Xaa
            20

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(3)
<223> OTHER INFORMATION: This region may encompass the residues Leu,
      Asp-Leu, or Leu-Asp-Leu
<220> FEATURE:
<221> NAME/KEY: MOD_RES
<222> LOCATION: (6)..(6)
<223> OTHER INFORMATION: Glu, Gln or Asp
<220> FEATURE:
<221> NAME/KEY: MOD_RES
<222> LOCATION: (10)..(19)
<223> OTHER INFORMATION: Any amino acid and this region may encompass 0
      to 10 residues
<220> FEATURE:
<223> OTHER INFORMATION: See specification as filed for detailed
      description of substitutions and preferred embodiments

<400> SEQUENCE: 23

Xaa Xaa Xaa Asp Leu Xaa Leu Arg Leu Xaa Xaa Xaa Xaa Xaa Xaa Xaa
1               5                   10                  15

Xaa Xaa Xaa

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Glu, Gln or Asp

<400> SEQUENCE: 24

Asp Leu Xaa Leu Arg Leu
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Asn, Glu, Gln, Thr or Ser
<220> FEATURE:
<221> NAME/KEY: MOD_RES
<222> LOCATION: (3)..(3)
<223> OTHER INFORMATION: Asp, Gln, Asn, Arg, Glu, Thr, Ser or His
<220> FEATURE:
<221> NAME/KEY: MOD_RES
<222> LOCATION: (5)..(5)
<223> OTHER INFORMATION: Arg, Gln, Asn, Thr, Ser, His, Lys or Asp

<400> SEQUENCE: 25

Xaa Leu Xaa Leu Xaa Leu
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Asp, Asn, Glu, Gln, Thr or Ser
<220> FEATURE:
<221> NAME/KEY: MOD_RES
<222> LOCATION: (3)..(3)
<223> OTHER INFORMATION: Asp, Gln, Asn, Arg, Glu, Thr, Ser or His
<220> FEATURE:
<221> NAME/KEY: MOD_RES
<222> LOCATION: (5)..(5)
<223> OTHER INFORMATION: Gln, Asn, Thr, Ser, His, Lys or Asp

<400> SEQUENCE: 26

Xaa Leu Xaa Leu Xaa Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Asn, Glu, Gln, Thr or Ser
<220> FEATURE:
<221> NAME/KEY: MOD_RES
<222> LOCATION: (3)..(3)
<223> OTHER INFORMATION: Asn, Arg, Thr, Ser or His

<400> SEQUENCE: 27

Xaa Leu Xaa Leu Arg Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Glu, Gln, Thr or Ser
<220> FEATURE:
<221> NAME/KEY: MOD_RES
<222> LOCATION: (3)..(3)
<223> OTHER INFORMATION: Asp, Gln, Asn, Arg, Glu, Thr, Ser or His

<400> SEQUENCE: 28

Xaa Leu Xaa Leu Arg Leu
1               5

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Leu Asp Leu Asp Leu Glu Leu Arg Leu Gly Phe Ala
1               5                   10
```

GENE THAT INCREASES PRODUCTION OF PLANT FAT-AND-OIL AND METHOD FOR USING THE SAME

CROSS REFERENCE TO RELATED APPLICATIONS

This application is a National Stage of International Application No. PCT/JP2009/053960 filed Mar. 3, 2009, claiming priority based on Japanese Patent Application No. 2008-054008 filed Mar. 4, 2008, the contents of all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Sep. 24, 2010, is named Q120597.txt and is 49,521 bytes in size.

BACKGROUND ART

The term "biomass" generally refers to the total amount of organic material that inhabits or exists in a given area. When such term is used for plants, in particular, it refers to dry weight per unit area. A biomass unit is quantified in terms of a mass or an energy amount. In the case of plant biomass, the term "standing crop" is occasionally used to represent "biomass." Since plant biomass is generated by fixing atmospheric carbon dioxide with the use of solar energy, it can be regarded as so-called "carbon-neutral energy." Accordingly, an increase in the amount of plant biomass is effective for global environmental protection, the prevention of global warming, and mitigation of greenhouse gas emissions. Thus, a technique for increasing the production of plant biomass is industrially significant.

Plants are cultivated for the purpose of using some tissue thereof (e.g., seeds, roots, leaves, or stems) or for the purpose of producing various materials, such as fat-and-oils. Examples of fat-and-oils produced from plants that have been heretofore known include soybean oil, sesame oil, olive oil, coconut oil, rice oil, cottonseed oil, sunflower oil, corn oil, safflower oil, palm oil, and rapeseed oil. Such fat-and-oils are extensively used for household and industrial applications. Also, fat-and-oils produced from plants are used as starting materials for biodiesel fuels or bioplastics, and the applicability thereof is increasing for alternative energy to petroleum.

Under such circumstances, it is necessary for the industrial success of the production of fat-and-oils using plants that the amount of production per unit of cultivation area be improved. If the number of cultivated plants is assumed to be constant per unit of cultivation area, an improvement in the amount of fat-and-oil production per plant is found to be necessary. When fat-and-oils are extracted from seeds obtained from plants, an improvement in the amount of fat-and-oil production per plant can be achieved via techniques of, for example, improving the seed yield per plant or increasing the fat-and-oil content in seeds.

Techniques for increasing the amount of fat-and-oil production from plant seeds are broadly classified into techniques based on an improvement in cultivation methods and techniques based on the development of plant varieties that can increase the amount of fat-and-oil production. Techniques based on the development of plant varieties that can increase the amount of fat-and-oil production are roughly classified as conventional breeding techniques such as crossing and molecular breeding techniques involving gene recombination. As techniques for increasing the amount of fat-and-oil production via gene recombination, A) a method of modifying a system for synthesizing triacylglycerol (TAG) of seeds, which is a main component of plant fat-and-oils, and B) a method of modifying a regulator gene that regulates plant morphogenesis or metabolism and expression of genes associated therewith are known.

In method A) above, the amount of TAG synthesized from a sugar produced via photosynthesis can be increased by (1) enhancing synthesis activity from a fatty acid or glycerol (i.e., TAG components) from sugars or (2) reinforcing the reaction of synthesizing TAG from glycerol and a fatty acid. In this regard, the following techniques have been reported as techniques that use genetic engineering techniques. An example of (1) is a technique in which cytosolic acetyl-coenzyme A carboxylase (ACCase) of *Arabidopsis thaliana* is overexpressed in rapeseed plastids and the fat-and-oil content in seeds is improved by 5% (Plant Physiology, 1997, Vol. 11, pp. 75-81). An example of (2) is a technique of increasing fat-and-oil production via overexpression of diacylglycerol acyltransferase (DGAT), which transfers an acyl group to the sn-3 position of diacylglycerol (Plant Physiology, 2001, Vol. 126, pp. 861-874). It is reported that the fat-and-oil content and the seed weight are increased as the DGAT expression level increases, and the number of seeds per plant may be occasionally increased according to the method of Plant Physiology, 2001, Vol. 126, pp. 861-874. The fat-and-oil content in *Arabidopsis thaliana* seeds was increased by 46% and the fat-and-oil amount per plant was increased by a maximum of about 125% by such technique.

As a form of method B), expression of transcriptional factor genes associated with the regulation of biosynthetic enzyme gene expression may be regulated. An example thereof can be found in WO 01/36597. WO 01/36597 employs a technique in which recombinant plants are prepared via exhaustive overexpression or knocking out of transcriptional factors and genes that enhance the fat-and-oil content in seeds are then selected. WO 01/36597 discloses that overexpression of ERF subfamily B-4 transcriptional factor genes results in a 23% increase in the fat-and-oil content in seeds. WO 01/36597, however, does not disclose an increase or decrease in fat-and-oil content per plant. Also, Plant J., 2004, 40, 575-585 discloses that the overexpression of WRINKLED1, which is a transcriptional factor having the AP2/EREB domain, improves the fat-and-oil content in seeds.

Although molecular breeding techniques as described above intended for the improvement of various traits have been developed, techniques for improving the yield involving increasing plant weight, increasing a given tissue, or improving the amount of target substances produced have not yet been put to practical use.

This is considered to be due to the following reasons. That is, truly adequate genes have not yet been discovered, and new recombinant varieties that are found effective at the test phase are unable to exhibit expected effects during the practical phase under a variety of natural environments. Also, many genes are associated with quantitative traits, such as increased plant weight, increased weight of a given tissue, or the amount of target substances produced, in various steps from those involving the control system to those involving the metabolic system, and it was difficult to discover and develop a truly adequate and useful gene that improves quantitative traits. In order to overcome such problems, the discovery of dramatically effective new genes and the development of genes exhibiting effects under practical environments, even if the effectiveness thereof is equivalent to that of existing genes, are necessary.

DISCLOSURE OF THE INVENTION

Object to be Attained by the Invention

Under given circumstances, it is an object of the present invention to search for a gene having a novel function of improving the amount of substances produced per individual plant, and particularly of improving the fat-and-oil content in seeds. Also, it is another object to provide a technique that can improve such properties of plants.

Means for Attaining the Object

The present inventors have conducted concentrated studies in order to attain the above objects. As a result, they discovered that expression of a chimeric protein resulting from the fusion of a transcription factor belonging a given transcription factor family with a functional peptide that converts an arbitrary transcription factor into a transcription repressor (hereafter it may be referred to as a "repressor domain") would improve a variety of quantitative traits, particularly the amount of substances produced per individual plant, and more particularly the amount of fat-and-oils produced. This has led to the completion of the present invention.

The plant of the present invention is obtained by expressing a chimeric protein resulting from the fusion of a transcription factor belonging a transcription factor family that includes a protein comprising the amino acid sequence as shown in SEQ ID NO: 4 with a functional peptide that converts an arbitrary transcription factor into a transcription repressor. In the plant of the present invention, transcription regulating activity, and particularly transcription accelerating activity, is preferably suppressed in a given transcription factor via fusion of a functional peptide.

The transcription factor that fuses the above functional peptide is preferably any of proteins (a) to (c) below:

(a) a protein comprising the amino acid sequence as shown in SEQ ID NO: 4;

(b) a protein comprising an amino acid sequence derived from the amino acid sequence as shown in SEQ ID NO: 4 by deletion, substitution, addition, or insertion of 1 or a plurality of amino acids and having transcription accelerating activity; or (c) a protein encoded by a polynucleotide hybridizing under stringent conditions to a polynucleotide comprising a nucleotide sequence complementary to the nucleotide sequence as shown in SEQ ID NO: 3 and having transcription accelerating activity.

Examples of the functional peptides include peptides represented by formulae (1) to (8) below:

(1) X1-Leu-Asp-Leu-X2-Leu-X3    (SEQ ID NO: 21)

wherein X1 represents 0 to 10 amino acid residues; X2 represents Asn or Glu; and X3 represents at least 6 amino acid residues;

(2) Y1-Phe-Asp-Leu-Asn-Y2-Y3    (SEQ ID NO: 22)

wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3    (SEQ ID NO: 23)

wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu    (SEQ ID NO: 24)

wherein Z4 represents Glu, Gln, or Asp;

(5) α1-Leu-β1-Leu-γ1-Leu;    (SEQ ID NO: 25)

(6) α1-Leu-β1-Leu-γ2-Leu;    (SEQ ID NO: 26)

(7) α1-Leu-β2-Leu-Arg-Leu;    (SEQ ID NO: 27)
and (8) α2-Leu-β1-Leu-Arg-Leu    (SEQ ID NO: 28)

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

A method for producing a substance with the use of the plant of the present invention comprises a step of separating and recovering a substance that can be produced in greater amounts from the plant of the present invention described above. An example of such substance is a fat-and-oil.

Further, the present inventors have conducted concentrated studies in order to attain the above objects. As a result, they discovered that the amount of substances produced per individual plant, and particularly the amount of fat-and-oils produced, could be improved in a strain that defects a gene involving the pigment synthesis pathway, thereby completing the present invention. Examples of genes involving the pigment synthesis pathway include a gene encoding a factor associated with transportation of a substrate or product of metabolic reactions in the pigment synthesis pathway, a gene encoding an enzyme that catalyzes metabolic reactions in the pigment synthesis pathway, and a gene encoding an enzyme that catalyzes a reaction for preparing a locus for metabolic reactions in the pigment synthesis pathway. Further examples include genes that regulate expression of a gene encoding a factor associated with transportation of a substrate or product of metabolic reactions in the pigment synthesis pathway, a gene encoding an enzyme that catalyzes metabolic reactions in the pigment synthesis pathway, and a gene encoding an enzyme that catalyzes a reaction for preparing a locu for metabolic reactions in the pigment synthesis pathway.

Specifically, the method for producing plant-derived fat-and-oils of the present invention comprises a step of recovering fat-and-oil components from seeds extracted from plants lacking functions of at least one gene selected from the group consisting of the chalcone synthase gene, the chalcone isomerase gene, and the flavone-3-hydrase gene.

Also, a method for screening for a plant with enhanced fat-and-oil content of the present invention comprises a step of extracting seeds from a plant that is a target of evaluation regarding the fat-and-oil content in seeds, and a step of observing the seed-coat color of extracted seeds and determining that the fat-and-oil content in seeds is high when such color is closer to white.

Effects of the Invention

The plant of the present invention can produce greater amounts of substances per individual plant. With the use of the plant of the present invention, accordingly, the amount of target substances produced can be improved, and a target substance can be produced at low cost.

The method for producing plant-derived fat-and-oils of the present invention can improve the amount of fat-and-oils produced because of the significantly improved fat-and-oil content per unit amount of seeds of a plant that lacks functions of a given gene.

Further, the method for screening for a plant with enhanced fat-and-oil content of the present invention comprises evaluating the fat-and-oil content in seeds in a non-destructive manner. Thus, screening can be rapidly and easily carried out with the use of a small number of seeds.

This description includes part or all of the contents as disclosed in the description and/or drawings of Japanese Patent Application No. 2008-054008, which is a priority document of the present application.

BEST MODE FOR CARRYING OUT THE INVENTION

Figure 1:
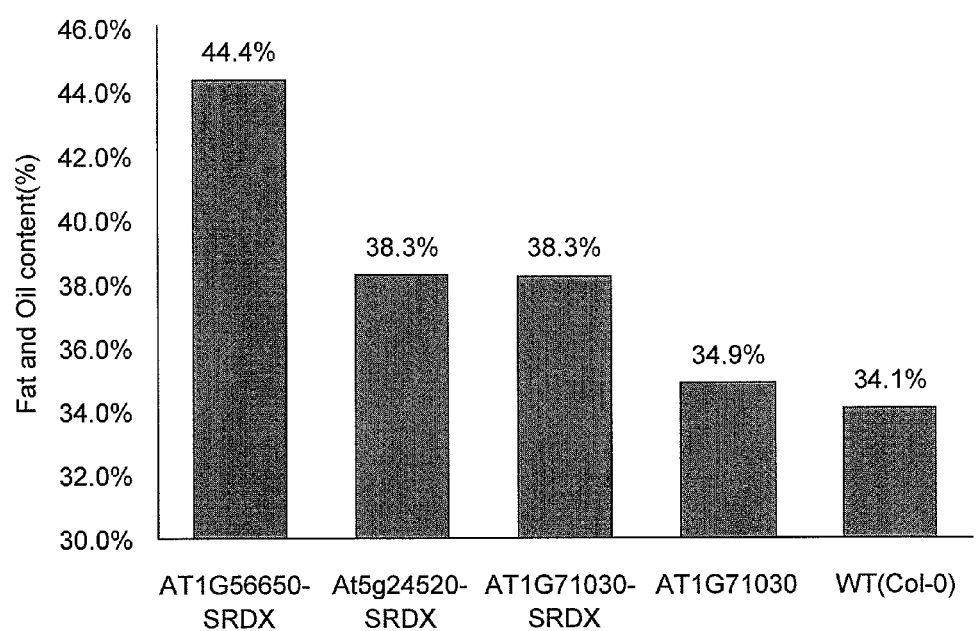
FIG. 1 is a characteristic diagram showing the results of measuring the fat-and-oil content in seeds of strains into which the modified transcription factor gene, improved transcription coactivator gene, or transcription factor gene had been introduced and those of wild-type strains.

Hereafter, the present invention is described in detail.

The plant of the present invention expresses a chimeric protein resulting from the fusion of a transcription regulator belonging a given transcription regulator family, particularly a transcription factor belonging a given transcription factor family, with a functional peptide that converts an arbitrary transcription factor into a transcription repressor, which can produce greater amounts of substances per individual plant compared with a wild-type plant. Specifically, the plant of the present invention expresses a chimeric protein of a transcription factor with the functional peptide, so as to significantly improve the amount of substances produced of a plant of interest.

In the plant of the present invention, in particular, the transcription accelerating activity according to a transcription factor is preferably suppressed via fusion with the functional peptide. In other words, it is preferable in the plant of the present invention for expression of a chimeric protein resulting from the fusion of a transcription factor with the functional peptide to result in the appearance of the transcription repression effects caused by the functional peptide as dominant traits.

The term "the amount of substances produced per individual plant" used herein refers to the contents of various substances generated from plants per unit volume. Substances are not particularly limited and may be naturally produced by plants. Alternatively, such substances may be not naturally produced by plants, but rather may be produced from plants via genetic engineering or other means. If the content of the target product per tissue is increased, in particular, purification and transportation costs can be reduced, and the industrial usefulness of such plants is significant. Specifically, target products may be lignocelluloses that account for substantially the entire weight of a plant, or plant oils that are used as seed oils at the industrial level may be used. Plant oil may be a simple lipid as an ester of fatty acid with alcohol, a complex lipid including phosphorus, sugar, nitrogen, and the like, or a fatty acid. An alcohol of a simple lipid may be a higher alcohol having a high molecular weight or a polyhydric alcohol, such as glycerol (glycerin). A fatty acid of a simple lipid may be a saturated fatty acid, unsaturated fatty acid, or special fatty acid comprising a hydroxyl group or an epoxy group. A simple lipid as the ester of glycerol and fatty acid may be monoacylglycerol, diacylglycerol, or triacylglycerol.

Hereafter, substances that can be produced in greater amounts are described with reference to fat-and-oils, although the technical scope of the present invention is not limited thereto. The present invention is also applicable to substances other than fat-and-oils as substances generated from plants.

Any plant can be the target of the present invention without particular limitation. Plants that have been heretofore used for the production of fat-and-oils are particularly preferable. Examples of plants that can serve as targets include soybeans, sesame, olive oils, coconuts, rice, cottons, sunflowers, maize, sugar cane, *Jatropha*, oil palm, tobacco, safflowers, and rapeseeds. Also, *Arabidopsis thaliana*, which is extensively used as a model organism in genetic analysis of plants and for which a method for gene expression analysis has been established can be a target plant.

Transcription repression activity according to a chimeric protein of a transcription factor refers to actively repressing expression of a gene located downstream by recognizing a cis sequence that is recognized by the transcription factor or recognizing another cis sequence recognized by other transcription factor similar to the former cis sequence. It may be referred to as a "transcription repressor." A method for repressing a transcription that is an activity according to the chimeric protein of the transcription factor is not particularly limited, but, most preferably, is a method for constructing a chimeric protein comprising a repressor domain sequence or an SRDX sequence (i.e., a fusion protein) is most preferable.

In such method, the term "repressor domain sequence" refers to an amino acid sequence constituting a peptide that converts an arbitrary transcription factor into a transcription repressor, and the present inventors have discovered various types of such sequence. Techniques involving the use of repressor domain sequences are disclosed in, for example, JP Patent Publication (kokai) No. 2001-269177 A, JP Patent Publication (kokai) No. 2001-269178 A, JP Patent Publication (kokai) No. 2001-292776 A, JP Patent Publication (kokai) No. 2001-292777 A, JP Patent Publication (kokai) No. 2001-269176 A, JP Patent Publication (kokai) No. 2001-269179 A, WO 03/055903, Ohta, M., Matsui, K., Hiratsu, K., Shinshi, H. and Ohme-Takagi, M., The Plant Cell, Vol. 13, 1959-1968, August, 2001, and Hiratsu, K., Ohta, M., Matsui, K., Ohme-Takagi, M., FEBS Letters 514, 2002, 351-354. Repressor domain sequences are cleaved from Class II ethylene-responsive element binding factor (ERF) proteins or plant zinc finger proteins (e.g., the *Arabidopsis thaliana* SUPERMAN protein) and have very simple structures.

An example of a transcription regulator expressed as a chimeric protein is the *Arabidopsis thaliana* transcription factor identified with the AGI code At1g71030 (hereafter simply referred to as the "transcription factor At1g71030"). The transcription factor At1g71030 is a transcription factor belonging the myb family, which is known to be similar to MybHv5 GI:19055 derived from barley. SEQ ID NO: 4 shows the amino acid sequence of the transcription factor At1g71030. SEQ ID NO: 3 shows the nucleotide sequence of the gene encoding the transcription factor At1g71030.

In addition, the transcription coactivator identified as At5g24520 (hereafter simply referred to as the "transcription coactivator At5g24520"), the transcription repressor, and the transcription corepressor are known as transcription regulators. A chimeric protein of such transcription coactivator or transcription repressor comprising a repressor domain can also be constructed. The factor identified with the AGI code At5g24520 is a transcription coactivator known as the transparent testa glabra 1 protein (TTG1). Regarding genes derived from other plants, a protein encoded by the Malus domestica-derived GenBank Accession Number AAF27919, a protein encoded by the *Petunia hybrida*-derived GenBank Accession Number AAC18914, a protein encoded by the *Gossypium hirsutum*-derived GenBank Accession Number AAM95645, and a protein encoded by the *Perilla frutescens*-derived GenBank Accession Number BAB58883 are known to be homologous to the transcription coactivator At5g24520, and such proteins are expected to exhibit functions equivalent to those described herein. SEQ ID NO: 2 shows the amino acid sequence of the transcription coactivator At5g24520. SEQ ID NO: 1 shows the nucleotide sequence of the gene encoding the transcription coactivator At5g24520.

The transcription coactivator At5g24520 and the transcription factor At1g71030, chimeric proteins of which are to be prepared, are not limited to those comprising the amino acid sequences as shown in SEQ ID NOs: 2 and 4. A transcription coactivator or transcription factor comprising an amino acid sequence derived from the amino acid sequence as shown in SEQ ID NO: 2 or 4 by deletion, substitution, addition, or insertion of 1 or a plurality of amino acids and having transcription accelerating activity may be used. The number of such plurality of amino acids is, for example, 1 to 20, preferably 1 to 10, more preferably 1 to 7, further preferably 1 to 5, and particularly preferably 1 to 3. Deletion, substitution, or addition of amino acids can be realized by modifying a nucleotide sequence encoding the above-mentioned transcription factor via a method known in the art. Mutation can be introduced into a nucleotide sequence via known methods, such as the Kunkel or Gapped duplex method, or methods in accordance therewith. For example, mutation is introduced with the use of mutagenesis kits utilizing site-directed mutagenesis (e.g., Mutant-K or Mutant-G (tradenames, manufactured by Takara Bio Inc.)) or the LA PCR in vitro Mutagenesis Series Kit (tradename, manufactured by Takara Bio Inc.). A mutation may be introduced via a method involving the use of chemical mutagens typified by EMS (ethyl methane sulfonate), 5-bromouracil, 2-aminopurine, hydroxylamine, N-methyl-N'-nitro-N-nitrosoguanidine, or other carcinogenic compounds, radiation processing typified by the use of x-rays, alpha rays, beta rays, gamma rays, or ion beams, or ultrasonic processing.

Further, transcription coactivators and transcription factors, chimeric proteins of which are to be prepared, are not limited to *Arabidopsis thaliana* transcription coactivator At5g24520 and transcription factor At1g71030. Transcription coactivators and transcription factors having equivalent functions in plants other than *Arabidopsis thaliana* (e.g., plants mentioned above) are included (hereafter referred to as "homologous transcription coactivator(s)" or "homologous transcription factor(s)"). Transcription coactivators homologous to the transcription coactivator At5g24520 or transcription factors homologous to the transcription factor At1g71030 can be searched for using the genome information of a target plant based on the amino acid sequences of the transcription coactivator At5g24520 or the transcription factor At1g71030 or the nucleotide sequences of such genes, if the plant genome information has been revealed. As a homologous coactivator and a transcription factor, an amino acid sequence having, for example, 70% or higher, preferably 80% or higher, more preferably 90% or higher, and most preferably 95% or higher homology to the amino acid sequence of the transcription coactivator At5g24520 or the transcription factor At1g71030 is searched for. Homology values are determined by default using a computer program that implements the BLAST algorithm and a database that stores gene sequence information.

When the plant genome information has not been revealed, the genome is extracted from the target plant, or a cDNA library of the target plant is constructed. The genome region or cDNA hybridizing under stringent conditions to at least part of the nucleotide sequence of the transcription coactivator At5g24520 or the transcription factor At1g71030 is then isolated. Thus, a homologous gene can be identified. Under stringent conditions, a so-called specific hybrid is formed, but a non-specific hybrid is not formed. For example, hybridization is carried out at 45° C. in the presence of 6×SSC (sodium chloride/sodium citrate), followed by washing at 50° C. to 60° C. in the presence of 0.2 to 1×SSC and 0.1% SDS. Alternatively, hybridization is carried out at 65° C. to 70° C. in the presence of 1×SSC, followed by washing at 65° C. to 70° C. in the presence of 0.3×SSC. Hybridization can be carried out in accordance with a conventional technique, such as the method described in J. Sambrook et al. Molecular Cloning, A Laboratory Manual, 2nd Ed., Cold Spring Harbor Laboratory, 1989.

The plant of the present invention significantly improves the amount of fat-and-oil production via expression of a chimeric protein of a transcription factor with a functional peptide. Also, the plant of the present invention significantly improves the amount of fat-and-oil production when the chimeric protein of a transcription coactivator with a functional peptide is expressed. By expressing a chimeric protein, in particular, a target transcription factor is expressed while transcription accelerating activity is suppressed, transcription repressing activity for recognizing a cis sequence homologous to the cis sequence that is recognized by the target transcription factor is expressed, and affinity and specificity to other factors, nucleic acids, lipids, or saccharides of the target transcription factor and transcription coactivator is changed, and the amount of fat-and-oil production is thus significantly improved. In such plant, the endogenous transcription factor or transcription coactivator may be modified to prepare a chimeric protein thereof. Alternatively, a gene encoding a chimeric protein may be introduced and such gene may be expressed.

A preferable example of such technique is a technique comprising introducing a gene encoding a chimeric protein (i.e., a fusion protein) resulting from the fusion of the aforementioned transcription factor or transcription coactivator with a functional peptide that converts an arbitrary transcription factor into a transcription repressor and expressing such chimeric protein (i.e., fusion protein) therein.

The term "transcription factor with suppressed transcription accelerating activity" used herein refers to a transcription factor exhibiting significantly lower transcription accelerating activity than the transcription factor originally had, without particular limitation. Also, the term "a functional peptide that converts an arbitrary transcription factor into a transcription repressor" refers to a peptide that, when it is fused with an arbitrary transcription factor and converted into a chimeric protein, has a function of significantly lowering the transcription accelerating activity to a level below that the transcription factor originally had. (It may be occasionally referred to as a "transcription repressor converting peptide".) A "functional peptide that converts an arbitrary transcription factor into a transcription repressor" used herein is not particularly limited, and it is particularly preferable for a peptide to comprise an amino acid sequence known as a repressor domain sequence or SRDX sequence. Such transcription repressor converting peptide is described in detail in JP Patent Publication (kokai) No. 2005-204657 A, and all peptides disclosed therein can be used.

Examples of transcription repressor converting peptides include amino acid sequences represented by formulae (1) to (8) below:

(1) X1-Leu-Asp-Leu-X2-Leu-X3    (SEQ ID NO: 21)

wherein X1 represents 0 to 10 amino acid residues; X2 represents Asn or Glu; and X3 represents at least 6 amino acid residues;

(2) Y1-Phe-Asp-Leu-Asn-Y2-Y3    (SEQ ID NO: 22)

wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3    (SEQ ID NO: 23)

wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu    (SEQ ID NO: 24)

wherein Z4 represents Glu, Gln, or Asp;

(5) α1-Leu-β1-Leu-γ1-Leu;    (SEQ ID NO: 25)

(6) α1-Leu-β1-Leu-γ2-Leu;    (SEQ ID NO: 26)

(7) α1-Leu-β2-Leu-Arg-Leu;    (SEQ ID NO: 27)
and (8) α2-Leu-β1-Leu-Arg-Leu    (SEQ ID NO: 28)

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

Transcription Repressor Converting Peptide Represented by Formula (1)

The number of amino acid residues represented by X1 of the transcription repressor converting peptide represented by formula (1) may be 0 to 10. Specific types of amino acids that constitute the amino acid residues represented by X1 are not particularly limited, and any amino acid may be used. It is preferable that the number of amino acid residues represented by X1 be as small as possible from the viewpoint of ease of synthesis of the transcription repressor converting peptide represented by formula (1). Specifically, the number of amino acid residues represented by X1 is preferably 5 or less.

Also, the number of the amino acid residues represented by X3 of the transcription repressor converting peptide represented by formula (1) may be at least 6. Specific types of amino acids that constitute the amino acid residues represented by X3 are not particularly limited, and any amino acid may be used.

Transcription Repressor Converting Peptide Represented by Formula (2)

The number of the amino acid residues represented by Y1 of the transcription repressor converting peptide represented by formula (2) may be 0 to 10, as in the case of X1 of the transcription repressor converting peptide represented by formula (1). Also, specific types of amino acids that constitute the amino acid residues represented by Y1 are not particularly limited, and any amino acid may be used. Specifically, the number of amino acid residues represented by Y1 is preferably 5 or less.

Also, the number of the amino acid residues represented by Y3 of the transcription repressor converting peptide represented by formula (2) may be at least 6, as in the case of X3 of the transcription repressor converting peptide represented by formula (1). Also, specific types of amino acids that constitute the amino acid residues represented by Y3 are not particularly limited, and any amino acid may be used.

Transcription Repressor Converting Peptide Represented by Formula (3)

The amino acid residues represented by Z1 of the transcription repressor converting peptide represented by formula (3) comprise 1 to 3 Leu residues: i.e., Leu when the number of amino acids is 1; Asp-Leu when the number of amino acids is 2; and Leu-Asp-Leu when the number of amino acids is 3.

In contrast, the number of the amino acid residues represented by Z3 of the transcription repressor converting peptide represented by formula (3) may be 0 to 10. Also, specific types of amino acids that constitute the amino acid residues represented by Z3 are not particularly limited, and any amino acid may be used. Specifically, the number of amino acid residues represented by Z3 is preferably 5 or less. Specific examples of amino acid residues represented by Z3 include, but are not limited to, Gly, Gly-Phe-Phe, Gly-Phe-Ala, Gly-Tyr-Tyr, and Ala-Ala-Ala.

The number of amino acid residues constituting the entire transcription repressor converting peptide represented by formula (3) is not particularly limited. From the viewpoint of ease of synthesis, the number of amino acids is preferably 20 or less.

Transcription Repressor Converting Peptide Represented by Formula (4)

The transcription repressor converting peptide represented by formula (4) is a hexamer (6-mer) comprising 6 amino acid residues. When the amino acid residue represented by Z4 of the transcription repressor converting peptide represented by formula (4) is Glu, the amino acid sequence of interest is equivalent to the amino acid sequence composed of amino acids 196 to 201 of the *Arabidopsis thaliana* SUPERMAN protein (SUP protein).

Various types of transcription repressor converting peptides described above are fused with the aforementioned transcription factors or transcription coactivators to obtain chimeric proteins (i.e., fusion proteins), so that properties of such transcription factors or transcription coactivators can be modified. Specifically, the transcription repressor converting peptides may be fused with the aforementioned transcription factors or transcription coactivators to obtain chimeric proteins (i.e., fusion proteins), so that such transcription factors or transcription coactivators can be modified in the form of transcription repressors or negative transcription coactivators. Further, non-dominant transcription repressors can be modified in the form of dominant transcription repressors.

In addition, a fusion gene of a polynucleotide encoding the transcription repressor converting peptide and a gene encoding a transcription factor or transcription coactivator may be produced to obtain a chimeric protein (i.e., a fusion protein). Specifically, a polynucleotide encoding the transcription repressor converting peptide (referred to as a "transcription repressor converting polynucleotide") is ligated to a gene encoding the transcription factor or transcription coactivator to construct a fusion gene, and the resultant is then introduced into a plant cell. Thus, chimeric proteins (i.e., fusion proteins) can be produced. Specific nucleotide sequences of the transcription repressor converting polynucleotides are not particularly limited, and such polynucleotides may comprise nucleotide sequences corresponding to the amino acid sequences of the transcription repressor converting peptides based on genetic code. The transcription repressor converting polynucleotides may comprise nucleotide sequences that serve as ligation sites to be connected to the transcription factor genes, according to need. When the amino acid reading frame of the transcription repressor converting polynucleotide is not aligned with that of the transcription factor or coactivator gene, further, the polynucleotide may comprise an additional nucleotide sequence, so as to align the reading frames. Further, the polynucleotide may comprise various additional polypeptides, such as a polypeptide having a linker function for connecting the transcription factor or transcription coactivator to the transcription repressor converting peptide or a polypeptide for labeling the chimeric protein (i.e., fusion protein) with an epitope, such as His, Myc, or Flag. Further, the chimeric protein (i.e., fusion protein) may comprise a structure other than a polypeptide, such as a sugar chain or an isoprenoid group, according to need.

The method for producing the plant is not particularly limited, provided that the method comprises a step of producing a chimeric protein of the transcription factor or transcription coactivator with a transcription repressor converting peptide in a plant to improve the amount of fat-and-oils produced. An example thereof is a production method comprising steps of construction of an expression vector, transformation, and selection. Such steps are described in detail below.

Step of Constructing Expression Vector

A step of constructing an expression vector is not particularly limited, provided that a recombinant expression vector comprising the gene encoding the above-mentioned transcription factor or transcription coactivator, the transcription repressor converting polynucleotide, and a promoter is constructed. A variety of known vectors can be used as matrices for recombinant expression vectors. Examples of vectors that can be used include plasmid, phage, and cosmid vectors, and adequate vectors can be selected in accordance with the plant cells to which such vectors are introduced or methods of introduction into a cell. Specific examples include pBR322, pBR325, pUC19, pUC119, pBluescript, pBluescriptSK, and pBI vectors. When a vector is introduced into a plant by the *Agrobacterium* method, in particular, use of the pBI binary vector is preferable. Specific examples of pBI binary vectors include pBIG, pBIN19, pBI101, pBI121, and pBI221 vectors.

Promoters are not particularly limited, provided that such promoters can express a gene of interest in a plant. Known promoters are preferably used. Examples of such promoters include cauliflower mosaic virus 35S promoters (CaMV 35S), actin gene promoters, ubiquitin gene promoters, noparin synthase gene promoters, tobacco PR 1 a gene promoters, and ribulose-1,5-bisphosphate carboxylase/oxygenase small subunit promoters, napin gene promoters, and oleosin gene promoters in tomatoes. Among such promoters, cauliflower mosaic virus 35S promoters, actin gene promoters, and ubiquitin gene promoters are preferable. With the use of such promoters, arbitrary genes can be intensively expressed upon introduction of the resulting recombinant expression vector into plant cells. A promoter is ligated so as to express the fusion gene of the gene encoding the transcription factor or transcription coactivator and the transcription repressor converting polynucleotide, and the resultant may be introduced into the vector in that state. The specific structure of a recombinant expression vector is not particularly limited.

The recombinant expression vector may further comprise other DNA segments, in addition to the promoter and the fusion gene. Such other DNA segments are not particularly limited, and examples thereof include a terminator, a selection marker, an enhancer, and a nucleotide sequence for enhancing translation efficiency. Also, the recombinant expression vector may further comprise a T-DNA region. The T-DNA region can enhance the efficiency of gene introduction, particularly when introducing the recombinant expression vector into a plant with the use of *Agrobacterium*.

A transcription terminator is not particularly limited, provided that it functions as a transcription termination site, and a known terminator may be used. Specific examples of transcription terminators that can be preferably used include the transcription termination region of the noparin synthase gene (the Nos terminator) and the transcription termination region of the cauliflower mosaic virus 35S (the CaMV 35S terminator), with the Nos terminator being more preferable. The recombinant vector can be used to avoid the occurrence of phenomena such as synthesis of an unnecessarily long transcript after the introduction thereof into plant cells or a reduction in the plasmid copy number caused by a potent promoter by positioning a transcription terminator in an adequate site.

Drug-resistance genes can be used as selection markers for transformants, for example. Specific examples of such drug-resistance genes include drug-resistance genes that are resistant to hygromycin, bleomycin, kanamycin, gentamicin, and chloramphenicol. Plants that grow in a medium containing the above antibiotics may be selected with the use of such selection markers, so that transformed plants can be easily selected.

An example of a nucleotide sequence for enhancing translation efficiency is the omega sequence derived from the tobacco mosaic virus. This omega sequence may be located in the untranslational region (5' UTR) of the promoter to enhance the translation efficiency of the fusion gene. Thus, the recombinant expression vector can comprise a variety of DNA segments in accordance with its intended purposes.

Methods for constructing recombinant expression vectors are not particularly limited. The promoter, the gene encoding the transcription factor or transcription coactivator, the transcription repressor converting polynucleotide, and, according to need, other DNA segments may be introduced into an adequately selected matrix vector in a predetermined order. For example, the gene encoding the transcription factor may be ligated to the transcription repressor converting polynucleotide to construct a fusion gene, the fusion gene may then be ligated to the promoter (e.g., a transcription terminator according to need) to construct an expression cassette, and the resulting expression cassette may be introduced into the vector.

When constructing a chimeric gene (fusion gene) and an expression cassette, for example, cleavage sites of DNA segments are made to be protruding ends that are complementary to each other, such DNA segments are subjected to a reaction with the aid of ligation enzymes, and the order of such DNA segments can be determined. When an expression cassette comprises a terminator, the expression cassette may comprise the promoter, the chimeric gene, and the terminator, in that order from upstream. Also, the types of reagents used for constructing a recombinant expression vector (i.e., restriction enzymes or ligation enzymes) are not particularly limited, and commercially available products may be adequately selected and used.

Also, methods for growing the recombinant expression vector (i.e., methods of production) are not particularly limited, and known methods can be employed. In general, *E. coli* hosts may be used, and the recombinant expression vector may be grown therein. In such a case, preferable *E. coli* species may be selected in accordance with vector type.

Step of Transformation

The step of transformation that is carried out in the present invention comprises introducing the aforementioned fusion genes into a plant cell so as to express such genes therein with the aid of the recombinant expression vector. Methods of gene introduction into a plant cell with the aid of a recombinant expression vector (i.e., methods of transformation) are not particularly limited, and adequate known methods can be employed in accordance with a given plant cell. Specific examples of such methods include a method involving the use of *Agrobacterium* and a method involving direct introduction of a gene into a plant cell. Examples of methods involving the use of *Agrobacterium* that can be employed include methods described in Bechtold, E., Ellis, J., and Pelletier, G., 1993, *In Planta Agrobacterium*-mediated gene transfer by infiltration of adult *Arabidopsis* plants, C. R. Acad. Sci. Paris Sci. Vie, 316, 1194-1199 and Zyprian E., Kado C. L., *Agrobacterium*-mediated plant transformation by novel mini-T vectors in conjunction with a high-copy vir region helper plasmid, Plant Molecular Biology, 1990, 15 (2), 245-256.

Examples of methods involving direct introduction of a recombinant expression vector with DNA comprising the target gene into a plant cell include microinjection, electroporation, the polyethylene glycol method, the particle gun method, the protoplast fusion method, and the calcium phosphate method.

When the method involving direct introduction of DNA into a plant cell is employed, DNA comprising a transcription unit that is necessary for expression of a target gene, such as DNA comprising a promoter, a transcription terminator, or a target gene, is sufficient, and vector functions are not necessary. Also, DNA comprising a protein coding region of a target gene without a transcription unit may be used, provided that such DNA can be integrated into a host transcription unit and express the target gene therein.

Examples of plant cells into which DNA comprising the recombinant expression vector and the target gene or DNA comprising the target gene without the expression vector are to be introduced include tissue cells in plant organs such as flowers, leaves, and roots, calluses, and suspension cultured cells. According to the method for producing plants of the present invention, the recombinant expression vector may be adequately constructed in accordance with the type of plant to be produced. Alternatively, a general-purpose recombinant expression vector may be constructed in advance and it may be introduced into a plant cell. Specifically, the method for producing plants of the present invention may or may not comprise the step of constructing DNA used for transformation with the use of the recombinant expression vector.

Other Steps and Other Methods

The method for producing the plant of the present invention may comprise the above-described method of transformation. Further, the method may comprise a step of constructing DNA used for transformation with the use of a recombinant expression vector and other steps. Specifically, the method may comprise a step of selecting adequate transformants from transformed plants.

Methods of selection are not particularly limited. For example, transformants may be selected based on drug resistance, such as hygromycin-resistance, or based on the content of fat-and-oils in plants or arbitrary organs or tissues after the transformed plants have been grown. For example, transformants may be selected based on fat-and-oil content by quantifying the fat-and-oil components in seeds of the transformants in accordance with a conventional technique and comparing the quantified value with the fat-and-oil content in seeds of non-transformed plants (see the examples below).

According to the method for producing the plant of the present invention, the fusion gene is introduced into a plant. Thus, offspring plants exhibiting significantly improved fat-and-oil content can be obtained from such plant via sexual or asexual reproduction. Also, plant cells or reproductive materials, such as seeds, fruits, stocks, calluses, tubers, cut ears, or lumps, may be obtained from a plant or an offspring plant thereof, and a plant of interest can be mass-produced therefrom. The method for producing the plant of the present invention, accordingly, may comprise a step of growing the selected plant (i.e., a step of mass production).

The term "plant" used herein refers to a grown plant, a plant cell, a plant tissue, a callus, or a seed. According to the present invention, specifically, substances that can eventually grow into individual plants are regarded as plants. Plant cells can exist in various forms. Examples of such plant cells include suspension cultured cells, protoplasts, and leaf sections. Such plant cells may be grown and differentiated to obtain plants. Plants can be reproduced from plant cells via a known technique in accordance with plant cell type. The method for producing the plant of the present invention, accordingly, may comprise a step of reproducing plants from plant cells or the like.

The method for producing the plant of the present invention is not limited to a method in which transformation is carried out with the aid of a recombinant expression vector, and other methods may be employed. Specifically, a chimeric protein (i.e., a fusion protein) may be introduced into a plant, for example. In such a case, the chimeric protein (i.e., a fusion protein) may be introduced into a young plant so as to improve the fat-and-oil content in a site of a plant that is to be eventually used. Methods for introducing the chimeric protein (i.e., a fusion protein) are not particularly limited, and various known methods may be employed.

As described above, the present invention can provide a plant that can produce greater amounts of substances per individual plant compared with that of a wild-type plant via expression of a chimeric protein of a transcription factor belonging a given transcription factor family with a functional peptide. The present invention can also provide a plant that can produce greater amounts of substances per individual plant compared with a wild-type plant via expression of a chimeric protein of a given transcription coactivator with a functional peptide. When such chimeric protein is expressed in a plant, transcription accelerating activity of a target transcription factor may occasionally be suppressed, or transcription suppressing effects may be exhibited on a sequence homologous to the cis sequence that is recognized by the target transcription factor. Further, a chimeric protein occasionally acts on other factors, DNA, RNA, lipids, or saccharides having affinity with the target transcription factor or transcription coactivator so as to alter such affinity and specificity. Also, a chimeric protein may occasionally act so as to improve affinity of a substance that has no affinity with the target transcription factor. In the plant of the present invention, the transcription factor that is subjected to a chimeric protein, a transcription factor that recognizes a cis sequence homologous to the cis sequence recognized by the aforementioned transcription factor, a transcription factor homologous to the aforementioned transcription factor that is subjected to a chimeric protein, other factors having affinity with the aforementioned transcription factor that is subjected to a chimeric protein, or the like is also expressed therein. However, expression of the target gene can be suppressed in a dominant-negative manner by the effects of the chimeric protein. This alters the expression levels of genes involved in fat-and-oil production and/or genes involved in decomposition of the produced fat-and-oils in the plant of the present invention. This is considered to result in the significantly enhanced fat-and-oil content.

The term "significantly enhanced fat-and-oil content" refers to a situation in which an amount of the fat-and-oil has been enhanced, although seed mass per grain has not changed compared with wild-type plants, a situation in which an amount of the fat-and-oil has been enhanced with significantly increased seed mass per grain compared with wild-type plants, or a situation in which the fat-and-oil content in seeds is enhanced compared with wild-type plants. All cases indicate increased amounts of fat-and-oils produced by an individual plant. The plant of the present invention can be used for the method for producing plant-derived fat-and-oils. For example, the plant of the present invention is allowed to grow, seeds are collected, and fat-and-oil components are extracted from the collected seeds. Thus, fat-and-oils can be produced.

It can be said that the method for producing fat-and-oils utilizing the plant of the present invention is particularly excellent in terms of the amount of production because of the high fat-and-oil content in an individual plant. If the number of cultivated plants is assumed to be constant per unit of cultivation area, specifically, the amount of fat-and-oils produced per unit of cultivation area is significantly increased with the use of the plant of the present invention. With the use of the plant of the present invention, accordingly, production costs required for the production of fat-and-oils can be remarkably reduced.

Further, the method for producing fat-and-oils with the use of the plant of the present invention realizes high fat-and-oil content in seeds per unit weight. Thus, the method can be said to be excellent in terms of the amount of fat-and-oil production.

In the method for producing fat-and-oils using the plant of the present invention, fat-and-oils to be produced are not particularly limited. Examples thereof include plant-derived fat-and-oils, such as soybean oil, sesame oil, olive oil, coconut oil, rice oil, cottonseed oil, sunflower oil, corn oil, safflower oil, and rapeseed oil. The produced fat-and-oils can be extensively used for household or industrial applications. Further, such fat-and-oils can be used as starting materials for biodiesel fuels. With the use of the plant of the present invention, specifically, such fat-and-oils for household or industrial applications, biodiesel fuels, and the like can be produced at low cost.

Method for Producing Plant-derived Fat-and-oils

According to the present invention, it was discovered that the fat-and-oil content was significantly improved in seeds extracted from a plant exhibiting a certain type of phenotype. Specifically, seeds extracted from 4 types of pigment synthesis pathway-deficient strains (i.e., tt4, tt5, tt6, and ACHS strains) disclosed in a reference document (Plant J., November 1995, 8 (5): 659-71) exhibit significantly improved fat-and-oil content in seeds compared with seeds extracted from wild-type plants. Specifically, the method for producing plant-derived fat-and-oils of the present invention comprises a step of recovering a fat-and-oil component from seeds extracted from a plant that lacks functions of at least 1 gene selected from the group consisting of the chalcone synthase gene, the chalcone isomerase gene, and the flavone-3-hydrase gene. The tt4 and the ACHS strains disclosed in the above document defect the chalcone synthase gene, the tt5 strain defects the chalcone isomerase gene, and the tt6 strain defects the flavone-3-hydrase gene.

SEQ ID NO: 5 shows the nucleotide sequence of the *Arabidopsis thaliana* chalcone synthase gene, and SEQ ID NO: 6 shows the amino acid sequence of chalcone synthase encoded by such gene. SEQ ID NO: 7 shows the nucleotide sequence of the *Arabidopsis thaliana* chalcone isomerase gene, and SEQ ID NO: 8 shows the amino acid sequence of chalcone isomerase encoded by such gene. SEQ ID NO: 9 shows the nucleotide sequence of the *Arabidopsis thaliana* flavone-3-hydrase gene, and SEQ ID NO: 10 shows the amino acid sequence of the flavone-3-hydrase encoded by such gene.

In the present invention, the chalcone synthase gene, the chalcone isomerase gene, and the flavone-3-hydrase gene are not limited to those comprising the sequences specifically described above. Specifically, the chalcone synthase gene, the chalcone isomerase gene, and the flavone-3-hydrase gene may each encode a protein comprising an amino acid sequence derived from the amino acid sequence specifically described above by deletion, substitution, addition, or insertion of 1 or a plurality of amino acids and having chalcone synthase activity, chalcone isomerase activity, and flavone-3-hydrase activity. The number of such plurality of amino acids is, for example, 1 to 20, preferably 1 to 10, more preferably 1 to 7, further preferably 1 to 5, and particularly preferably 1 to 3. Deletion, substitution, or addition of amino acids can be realized by modifying the nucleotide sequence specifically described above via a method known in the art. Mutation can be introduced into a nucleotide sequence via known methods, such as the Kunkel or Gapped duplex method, or methods in accordance therewith. For example, mutation is introduced with the use of mutagenesis kits utilizing site-directed mutagenesis (e.g., Mutant-K or Mutant-G (tradenames, manufactured by Takara Bio Inc.)) or the LA PCR in vitro Mutagenesis Series Kit (tradename, manufactured by Takara Bio Inc.). A mutation may be introduced via a method involving the use of chemical mutagens typified by EMS (ethyl methane sulfonate), 5-bromouracil, 2-aminopurine, hydroxylamine, N-methyl-N'-nitro-N-nitrosoguanidine, or other carcinogenic compounds, radiation processing typified by the use of x-rays, alpha rays, beta rays, gamma rays, or ion beams, or ultrasonic processing.

In the present invention, the chalcone synthase gene, the chalcone isomerase gene, and the flavone-3-hydrase gene further comprise genes having equivalent functions in plants other than *Arabidopsis thaliana* (e.g., plants described above) (hereafter such genes are referred to as "homologous genes"). Homologous genes of the chalcone synthase gene, the chalcone isomerase gene, or the flavone-3-hydrase gene can be searched for using plant genome information of the target plant based on the nucleotide sequence of the chalcone synthase gene, the chalcone isomerase gene, or the flavone-3-hydrase gene or the amino acid sequence encoded thereby, if the plant genome information has been revealed. As a homologous transcription factor, an amino acid sequence having, for example, 70% or higher, preferably 80% or higher, more preferably 90% or higher, and most preferably 95% or higher homology to the amino acid sequence specifically described above is searched for. Homology values are determined by default using a computer program that implements the BLAST algorithm and a database that stores gene sequence information.

When the plant genome information has not been revealed, the genome is extracted from the target plant, or a cDNA library of the target plant is constructed. The genome region or cDNA hybridizing under stringent conditions to at least part of the nucleotide sequence of the chalcone synthase gene, the chalcone isomerase gene, or the flavone-3-hydrase gene is then isolated. Thus, a homologous gene can be identified. Under stringent conditions, a so-called specific hybrid is formed, but a non-specific hybrid is not formed. For example, hybridization is carried out at 45° C. in the presence of 6×SSC (sodium chloride/sodium citrate), followed by washing at 50° C. to 65° C. in the presence of 0.2 to 1×SSC and 0.1% SDS. Alternatively, hybridization is carried out at 65° C. to 70° C. in the presence of 1×SSC, followed by washing at 65° C. to 70° C. in the presence of 0.3×SSC. Hybridization can be carried out in accordance with a conventional technique, such as the method described in J. Sambrook et al. Molecular Cloning, A Laboratory Manual, 2nd Ed., Cold Spring Harbor Laboratory, 1989.

In other words, application of the method for producing plant-derived fat-and-oils of the present invention is not limited to a system involving the use of *Arabidopsis thaliana*-derived seeds, and the method is applicable to any type of plant. Examples of plants to which the method for producing plant-derived fat-and-oils of the present invention can be applied include, but are not limited to, dicotyledonous plants and monocotyledonous plants, such as plants of *Brassicaceae, Gramineae, Solanaceae, Leguminosae,* and *Salicaceae* (see below).

Examples of *Brassicaceae* plants include *Arabidopsis thaliana,* oilseed rape (*Brassica rapa* and *Brassica napus*), cabbage (*Brassica oleracea* var. *capitata*), rapeseed (*Brassica rapa* and *Brassica napus*), field mustard (*Brassica rapa* and *Brassica napus*), *Brassica pekinensis* (*Brassica rapa* var. *pekinensis*), bok choy (*Brassica rapa* var. *chinensis*), turnip (*Brassica rapa* var. *rapa*), *Brassica rapa* var. *hakabura*, *Brassica rapa* var. *lancinifolia*, *Brassica rapa* var. *peruviridis*, pak Choi (*Brassica rapa* var. *chinensis*), Japanese radish (*Brassica Raphanus sativus*), and horseradish (*Wasabia japonica*).

Examples of Solanaceae plants include tobacco plants (*Nicotiana tabacum*), eggplants (*Solanum melongena*), potatoes (*Solaneum tuberosum*), tomatoes (*Lycopersicon lycopersicum*), capsicum (*Capsicum annuum*), and *Petunia* plants.

Examples of Leguminosae plants include soybeans (*Glycine max*), peas (*Pisum sativum*), horse beans (*Vicia faba*), *Wisteria floribunda*, peanuts (*Arachis. hypogaea*), bird's-foot trefoils (*Lotus corniculatus* var. *japonicus*), bush beans (*Phaseolus vulgaris*), azuki beans (*Vigna angularis*), and Acacia plants.

Examples of Compositae plants include chrysanthemums (*Chrysanthemum morifolium*) and sunflowers (*Helianthus annuus*).

Examples of Arecaceae plants include *Elaeis guineensis* (or *Elaeis oleifera*), *Cocos nucifera, Phoenix dactylifera,* and *Copernicia.*

Examples of Anacardiaceae plants include *Rhus succedanea, Anacardium occidentale, Toxicodendron vernicifluum, Mangifera indica,* and pistachios (*Pistacia vera*).

Examples of Cucurbitaceae plants include pumpkins (*Cucurbita maxima, Cucurbita moschata,* or *Cucurbita pepo*), cucumbers (*Cucumis sativus*), *Trichosanthes cucumeroides,* and gourds (*Lagenaria siceraria* var. *gourda*).

Examples of Rosaceae plants include almonds (*Amygdalus communis*), roses (*Rosa*), strawberries (*Fragaria*), cherry trees (*Prunus*), and apples (*Malus pumila* var. *domestica*).

Examples of Caryophyllaceae plants include carnations (*Dianthus caryophyllus*).

Examples of Salicaceae plants include *Populus nigra* (*Populus trichocarpa, Populus nigra,* and *Populus tremula*).

Examples of Gramineae plants include maize (*Zea mays*), rice (*Oryza sativa*), barley (*Hordeum vulgare*), wheat (*Triticum aestivum*), bamboo (*Phyllostachys*), and sugarcane (*Saccharum officinarum*).

Examples of Liliaceae plants include tulips (*Tulipa*) and lilies (*Lilium*).

The phrase " . . . lack(s) functions of a gene . . . " refers to a situation in which the relevant gene has been deleted from the genome, in which expression of such gene has been inhibited (at the transcriptional and translational levels), and in which the activity of a protein encoded by such gene has been lowered or eliminated.

Specifically, methods for disrupting a gene of interest are not particularly limited, and examples include a method involving homologous recombination and a method involving the use of transposon. When such gene is to be deleted, the full length of such gene may be deleted, or part thereof may be deleted.

Examples of methods for inhibiting gene expression include, but are not particularly limited to, a method in which a promoter that regulates expression of the gene of interest is deleted, a method in which a promoter that regulates expression of the gene is substituted with an expression-inducible promoter, a method in which a mutation is introduced into a promoter that regulates expression of the gene, a method in which the gene transcript is degraded with the use of RNA interference, and a method in which translation of the gene is inhibited with the use of antisense RNA.

An example of a method for lowering activity of a protein encoded by the gene of interest is a method in which a substance that specifically binds to a protein of interest to suppress activity thereof is allowed to undergo a reaction. Examples of such substance include an antibody and an inhibitor that can inhibit functions of the protein.

In the method for producing plant-derived fat-and-oils of the present invention, fat-and-oils may be recovered from seeds via, for example, compression, extraction, or expulsion, without particular limitation. For example, fat-and-oil components can be recovered from seeds extracted from plants via ether extraction with the use of a Soxhlet extractor. The method for producing plant-derived fat-and-oils of the present invention involves the use of a plant with higher fat-and-oil content per seed grain, even when the amounts of seeds extracted from individual plants are equivalent. Thus, it can be said that the method of the present invention is excellent in terms of the amount of fat-and-oil production. If the number of individual plants cultivated per unit of cultivation area were constant, in other words, the method for producing plant-derived fat-and-oils of the present invention can significantly improve the fat-and-oil content prepared per unit of cultivation area, which can remarkably decrease the production cost required for fat-and-oil production.

In the method for producing plant-derived fat-and-oils of the present invention, fat-and-oils can be prepared from any plants without particular limitation. Examples include fat-and-oils derived from plants such as soybean oil, sesame oil, olive oil, coconut oil, rice oil, cottonseed oil, sunflower oil, corn oil, safflower oil, and rapeseed oil. In addition, produced fat-and-oils can be extensively utilized for household or industrial applications, and such fat-and-oils can be utilized as starting materials of biodiesel fuels or bioplastics. With the use of the plant of the present invention, specifically, fat-and-oils utilized for household or industrial applications, biodiesel fuels, bioplastics, or the like can be produced at low cost.

Method for Screening for Plant Exhibiting Enhanced Fat-and-oil Content

According to the present invention, it was discovered that fat-and-oil content was significantly improved in seeds extracted from a strain that lacks a pigment synthesis pathway (reference document: Plant J. November 1995; 8 (5): 659-71), compared with seeds extracted from a wild-type strain. In the pigment synthesis pathway-deficient strain, functions of a gene involved in a pigment synthesis system have been eliminated, and such strain exhibits the phenotype of a lighter seed-coat color (which is closer to white than that of a wild-type seed-coat) compared with a wild-type strain. The tt4 and the ACHS strains disclosed in the above document lack the chalcone synthase gene, the tt5 strain lacks the chalcone isomerase gene, and the tt6 strain lacks the flavone-3-hydrase gene. In mutant strains lacking such genes, seed-coat color becomes closer to white because of the failure of pigment synthesis. Thus, seeds may be extracted from plants to be screened for, and seed-coat color of the extracted seeds may be inspected, so that the capacity of the pigment synthesis pathway of the plants for pigment synthesis can be evaluated, and the content thereof in the extracted seeds can be deduced with high accuracy.

When a variety of plants of the same species are present, for example, the seed-coat color of seeds extracted from such plants is observed, and seeds having a color closer to white can be selected as seeds of a plant variety that can produce greater amounts of fat-and-oils. Plants to be screened for may be those obtained via some sort of mutagen treatment or plant varieties prepared via conventional breeding techniques.

Mutagen treatment is not particularly limited, and it may be carried out with the use of a chemical mutagen and/or physical mutagen extensively used for mutagenesis. Examples of chemical mutagens that can be used include ethyl methane sulfonate (EMS), ethylnitrosourea (ENS), 2-aminopurine, 5-bromouracil (5-BU), and an alkylation agent. Examples of physical mutagens that can be used include radioactive rays and ultraviolet rays. Mutagenesis with the use of such mutagens can be carried out by a known method.

According to the screening method of the present invention, the fat-and-oil content in seeds can be determined in a very simple and rapid manner by visually observing seed-coat color without the need to destroy seeds extracted from plants.

According to the screening method of the present invention, also, the seed-coat color of seeds extracted from plants may be determined based on image data and quantitatively assayed. More specifically, the image of the seed to be evaluated is converted into digital data, and the R, G, and B values (i.e., the RGB value) in the seed region in the image data are assayed. The R, G, and B values in the seed region may be assayed with the use of any type of image-processing software. Subsequently, the assayed R, G, and B values are compared with the R, G, and B values in seeds extracted from a wild-type plant. For example, the integrated value of the assayed R, G, and B values is determined and compared with that of seeds extracted from a wild-type plant. If the integrated value of the assayed R, G, and B values is significantly higher than that of seeds extracted from a wild-type plant, for example, the seed-coat color of the seed to be evaluated can be determined to be closer to white. When the integrated value of the assayed R, G, and B values is 2.88 or more times as high as that of seeds extracted from a wild-type plant, in particular, the seed can be determined to have a color closer to white (i.e., to be more pale in color).

As described above, the fat-and-oil content in seeds can be determined in a very simple and rapid manner without the need for destroying seeds, even with a technique of observing the seed-coat color of a seed extracted from a plant as image data. When observing the seed-coat color of a seed in image data, the sum of the R, G, and B values or the like may be calculated, in addition to the integrated value of the R, G, and B values.

EXAMPLES

Hereafter, the present invention is described in greater detail with reference to the examples, although the technical scope of the present invention is not limited to the examples.

Example 1

In this example, chimeric proteins (i.e., fusion proteins) of the *Arabidopsis thaliana* transcription coactivator At5g24520 and transcription factor At1g71030 to which repressor domain sequences had been added were expressed in plants, and the fat-and-oil content in seeds obtained from the plants was measured. For comparison, a chimeric protein (i.e., a fusion protein) of the transcription factor At1g56650 was expressed in a plant in the same manner, and the fat-and-oil content in seeds was assayed.

Amplification of Transcription Factor Gene

A DNA fragment of a coding region of At1g71030 excluding the termination codon thereof, a DNA fragment of a coding region of At1g71030 including the termination codon thereof, a DNA fragment of a coding region of At5g24520 excluding the termination codon thereof, and a DNA fragment of a coding region of At1g56650 excluding the termination codon thereof were obtained from the *Arabidopsis thaliana* cDNA library, and the DNA fragments were amplified via PCR using the primers shown below. PCR was carried out via denaturation at 94° C. for 1 minute, annealing at 47° C. for 2 minutes, and elongation at 74° C. for 1 minute, and this cycle was repeated 25 times. After the completion of PCR, the amplified DNA fragments were separated via agarose gel electrophoresis and recovered.

```
Forward primer 1 for amplifying At1g71030
                                   (SEQID NO: 11)
gATGAACAAAACCCGCCTTCGTGCTCTCTC Reverse primer 1 for amplifying At1g71030
                                   (SEQID NO: 12)
TCGGAATAGAAGAAGCGTTTCTTGACCTGT Forward primer 2 for amplifying At1g71030
                                   (SEQID NO: 13)
gATGAACAAAACCCGCCTTCGTGCTCTCTC Reverse primer 2 for amplifying At1g71030
                                   (SEQID NO: 14)
TCATCGGAATAGAAGAAGCGTTTCTTGACC Forward primer for amplifying At1g56650
                                   (SEQID NO: 15)
GATGGAGGGTTCGTCCAAAGGGC Reverse primer for amplifying At1g56650
                                   (SEQID NO: 16)
ATCAAATTTCACAGTCTCTCCATCG
```

```
Forward primer for amplifying At5g24520
                                    (SEQID NO: 17)
gATGGATAATTCAGCTCCAGATTCGTTATC Reverse primer for amplifying At5g24520
                                    (SEQID NO: 18)
AACTCTAAGGAGCTGCATTTTGTTAGCAAA
```

Preparation of Fusion Gene

In order to add the repressor domain sequence to the 3' terminus of the transcription factor gene encoded by the above DNA fragment, a p35SSXG vector having the SmaI site and the repressor domain (amino acid sequence: GLD-LDLELRLGFA) (SEQ ID NO: 29) sequence downstream of the CaMV35S promoter was used. In order to ligate the transcription factor gene sequence to the repressor domain sequence, the vector was cleaved with SmaI, and a PCR-amplified fragment encoding the above transcription factor was introduced to prepare P35SSXG (At1g56650), p35SSXG (At5g24520), and p35SSXG (At1g71030). The PCR-amplified fragment obtained with the use of the forward primer 1 for amplifying At1g71030 and the reverse primer 1 for amplifying At1g71030 was introduced into p35SSXG (At1g71030). In order to express the PCR-amplified fragment obtained with the use of the forward primer 2 for amplifying At1g71030 and the reverse primer 2 for amplifying At1g71030 without the addition of the repressor domain, a p35SOXG vector having the SmaI site sequence downstream of the CaMV35S promoter was introduced into the SmaI-cleavage site to prepare p35SOXG (At1g71030).

Construction of Modified Transcription Factor and Transcription Factor Expression Vector A pBCKH binary vector was used in order to introduce a gene into a plant by the *Agrobacterium* method. This vector was prepared by incorporating a cassette of the Gateway vector conversion system (Invitrogen) into the HindIII site of pBIG (Hygr) (Nucleic Acids Res. 18, 203, 1990). In order to incorporate the modified transcription factor gene into this vector, the vector was mixed with p35SSXG (At1g56650), p35SSXG (At5g24520), p35SSXG (At1g71030), or p35SOXG (At1g71030), and a recombination reaction was carried out using GATEWAY LR clonase (Invitrogen). As a result, pBCKH-p35SSXG (At1g56650), pBCKH-p35SSXG (At5g24520), pBCKH-p35SSXG (At1g71030), and pBCKH-p35SOXG (At1g71030) were constructed.

Introduction of Expression Vector for Modified Transcription Factor Gene Into Plant

*Arabidopsis thaliana*, Columbia was used as a plant into which the modified transcription factor was to be introduced. Gene introduction was carried out in accordance with the vacuum infiltration method of transformation of *Arabidopsis thaliana*. Plants were infected by being soaked in the *Agrobacterium* solution without depressurization. Specifically, expression vectors for modified transcription factors, pBCKH-p35SSXG (At1g56650), pBCKH-p35SSXG (At5g24520), pBCKH-p35SSXG (At1g71030), and pBCKH-p35SOXG (At1g71030), were introduced into soil bacteria (i.e., the *Agrobacterium tumefaciens* strain GV3101 (C58C1Rifr) pMP90 (Gmr)) (koncz and Schell, 1986) via electroporation.

The introduced bacteria were cultured in 1 liter of YEP medium containing antibiotics (50 μg/ml of kanamycin (Km), 25 μg/ml of gentamicin (Gm), and 50 μg/ml of rifampicin (Rif)) until OD600 reached 1. Subsequently, the bacteria were recovered from the culture solution and suspended in 1 liter of infiltration medium (containing 2.2 g of MS salt, 1× B5 vitamin, 50 g of sucrose, 0.5 g of MES, 0.044 μM of benzylaminopurine, and 400 μl of Silwet per liter; pH: 5.7). The *Arabidopsis thaliana* plant that had been grown for 14 days was soaked in this solution for 1 minute, the plant was infected, and culture was continued again for fructification. The resulting seeds (T1 seeds) were sterilized with a 50% bleach/0.02% Triton X-100 solution for 7 minutes, the seeds were rinsed three times with sterilized water, and the seeds were sowed on the sterilized hygromycin selection medium (4.3 g/l MS salt, 0.5% sucrose, 0.5 g/l MES (pH 5.7), 0.8% agar, 30 mg/l hygromycin, and 250 mg/l vancomycin). Ten transformed strains that had grown on the hygromycin plate (T1 plants) were selected per modified transcription gene and transferred to a pot (diameter: 50 mm) containing vermiculite composite soil. The transformants were cultivated at 22° C. for 16 hours in the light and 8 hours in the dark at an optical intensity of about 60 to 80 μE/cm² to obtain seeds (T2 seeds). The epidermis color of the obtained T2 seeds was light brown or yellow while that of the wild-type strain was dark brown.

Strain that Lacks Pigment Synthesis Pathway

In this example, the fat-and-oil content in seeds obtained from strains that lack the pigment synthesis pathway was measured. Specifically, seeds were obtained from strains that lack the pigment synthesis pathway; i.e., the tt4 strain (NASC stock No. N85) (reference: Plant J., 8, 659-671, 1995), the tt5 strain (NASC stock No. N86), the tt6 strain (NASC stock No. N87) (reference: Plant Physiol., 111, 339-345, 1996), and the ΔCHS strain (NASC stock No. N520583) (NASC: the Nottingham *Arabidopsis* Stock Centre). The tt4, tt5, and tt6 strains were prepared from the *Arabidopsis thaliana*, Ler strain, and the ΔCHS strain was prepared from the *Arabidopsis thaliana* Col-0 strain. The resulting seeds were sterilized with a 50% bleach/0.02% Triton X-100 solution for 7 minutes, rinsed three times with sterilized water, and sowed on a medium (4.3 g/l MS salt, 0.5% sucrose, 0.5 g/l MES (pH 5.7), 0.8% agar). The plants growing on the plate were transferred to a pot (diameter: 50 mm) containing vermiculite composite soil. The tt4, tt5, tt6, and WT (Ler) strains were cultivated at 22° C. for 16 hours in the light and 8 hours in the dark at an optical intensity of about 50 to 60 μE/cm², or the ΔCHS and WT (Col-o) strains were cultivated at an optical intensity of about 40 μE/cm² to obtain seeds. The epidermis color of the obtained seeds was light brown or yellow while that of the wild-type strain was dark brown.

Analysis of T2 Seeds Into Which Modified Transcription Factor or Transcription Factor had Been Introduced The fat-and-oil content of the T2 seeds into which either of the modified transcription factor gene or improved transcription coactivator gene had been introduced (i.e., (At1g56650-SRDX, At5g24520-SRDX, or At1g71030-SRDX), the T2 seeds into which a transcription factor had been introduced (i.e., At1g71030), and the wild-type seeds (Col-0 and Ler strains) were analyzed. Quantitative analysis of the fat-and-oil content in 2 to 10 mg of *Arabidopsis thaliana* seeds was carried out using MARAN-23 (Resonance Insturuments Ltd., UK)$^H$-NMR and the RI-NMR Ver. 2.0 analysis software. A calibration curve was prepared using olive oil as a fat-and-oil reference material, and the fat-and-oil content in seeds (% by weight) was determined.

Average values for the fat-and-oil content in seeds of strains into which the modified transcription factor genes, the improved transcription coactivators, or the transcription factor genes had been introduced and wild-type strains were determined (n=3 to 10). As a result, the percentages of fat-and-oil content increase when the average fat-and-oil content of Col-0 was designated as 1 were as follows: 30.2% in the T2 seeds (At1g56650-SRDX), 12.3% in the T2 seeds (At5g24520-SRDX), 12.2% in the T2 seeds (At1g71030-SRDX), and 2.3% in the T2 seeds (At1g71030) (FIG. 1)

Analysis of Seeds of Strain that Lacks Pigment Synthesis Pathway

The fat-and-oil content in four types of seeds of strains that lack the pigment synthesis pathway (i.e., tt4, tt5, tt6, and ΔCHS strains) and of wild-type strains (Col-0 and Ler strains) were analyzed. Quantitative analysis of the fat-and-oil content in 2 to 10 mg of *Arabidopsis thaliana* seeds was carried out using MARAN-23 (Resonance Insturuments Ltd., UK)[H]-NMR and the RI-NMR Ver. 2.0 analysis software. A calibration curve was prepared using olive oil as a fat-and-oil reference material and the fat-and-oil content in seeds (% by weight) was determined.

Figure 2:
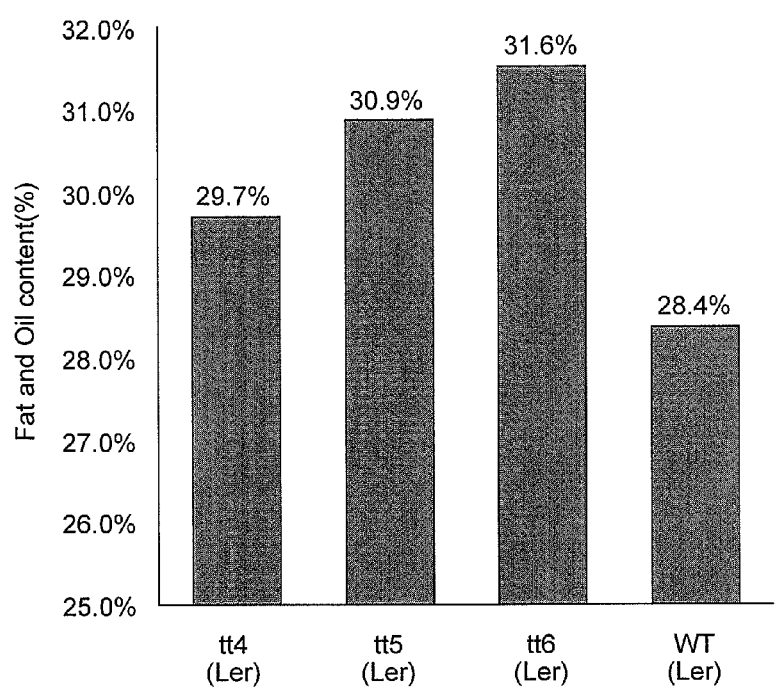
FIG. 2 is a characteristic diagram showing the results of measuring the fat-and-oil content in seeds of strains lacking the pigment synthesis pathway and of wild-type strains.

Average values of the fat-and-oil content in seeds of strains that lack a pigment synthesis pathway were determined (n=3 to 10). The fat-and-oil content of the ΔCHS strain was 8.9% relative to that of the Col-0 strains, and the fat-and-oil content of the tt4, tt5, and tt6 strains were 4.7%, 8.8%, and 11.1%, respectively, relative to that of the Ler strain (FIG. 2).

Results and Discussion

The above results demonstrate that the fat-and-oil content per seed weight of plants into which the chimeric genes of the transcription factor At1g56650, the transcription coactivator At5g24520, and the transcription factor At1g71030 each comprising the repressor domain had been introduced were higher than that per weight of wild-type strains that had been simultaneously cultivated, and such plants are very effective for fat-and-oil production. Fat-and-oil content per seed weight of the plant into which At1g71030 having expression accelerating activity had been introduced was somewhat increased compared with the fat-and-oil content per weight of the plant that had been simultaneously cultivated. However, the percentage of increase was about one-fifth the percentage of increase of the fat-and-oil content per weight of a plant seed into which At1g71030 with suppressed expression accelerating activity had been introduced. At1g71030 encodes a protein having a single MYB-like domain (AtMybL2) and overexpresses this gene with the aid of the CaMV35S promoter to show the traits of a lack of trichomes on leaves, stem, and calyx. This is considered to result from suppression of expression of the GL2 gene, which is necessary for trichome formation (reference: DNA Res., 9, 31-34, 2002). It is reported that disruption of the GL2 gene increases the fat-and-oil content in seeds by 8% (reference: Plant Mol Biol., 2006, 60, 377-87, 2006).

Also, the AtMybL2 protein has a transcription repressor comprising 6 amino acids at the carboxy terminus, and synthesis of an anthocyanin precursor was suppressed in a plant overexpressing the AtMybL2 gene and a plant overexpressing the gene encoding AtMybL2 to which a transcription repressor known as the EAR-motif had been added (reference: 18TH International Conference On Arabidopsis Research, TAIR accession Publication: 501721814). As a result of analysis, the percentage of increase in the fat-and-oil content in the T2 seeds obtained from At1g71030-overexpressing plants was 2.3%. The percentage of increase in the fat-and-oil content of the T2 seeds obtained from the At1g71030-overexpressing plant to which the repressor domain had been added was significantly high (i.e., 12.2%), which was remarkably high compared with the percentage of increase in the fat-and-oil content when the GL2 gene was disrupted (i.e., 8%). Based on these results, it is considered that the repressor domain-containing At1g71030 functions during the process of seed fat-and-oil synthesis and storage in unknown pathways other than GL2 and increases fat-and-oil content.

As a result of analysis of strains lacking the pigment synthesis pathway, the fat-and-oil content in seeds of the mutant strains tt4, tt5 and tt6, in which the major gene of the pigment synthesis pathway had been disrupted, and in seed of the ΔCHS strain in which the CHS gene had been disrupted upon insertion of T-DNA were higher than that in wild-type strains. Regarding the correlation between seed-coat color and fat-and-oil content, it is reported that the fat-and-oil content of the yellow-seeded rapeseed cultivar, HUA-yellow No. 1, is 5% to 7% higher than that of the black-seeded rapeseed cultivar (reference: Genome 44: 1077-1082, 2001). According to a conventional breeding technique resulting from inter-breeding, however, a similar phenomenon can be observed even when the loci of traits that determine the seed-coat color and the fat-and-oil content in seeds are adjacent to each other. Thus, the correlation between gene expression and traits has not yet been elucidated. Specifically, there was no finding regarding the influence of the gene locus that affects the trait of seed-coat color on fat-and-oil content in the past.

In the present invention, however, the gene encoding a pigment synthesis enzyme of a seed coat was actually disrupted, and an increase was observed in the fat-and-oil content in seeds. Thus, it was found for the first time that the seed-coat color is a critical phenotype for predicting the fat-and-oil content in the case of gene introduction or molecular breeding via gene disruption, in addition to conventional breeding via crossing. The use of a seed-coat color as an indicator enables efficient selection of seeds exhibiting increased fat-and-oil content in a non-destructive manner without the use of special equipment.

More specifically, seeds of wild-type strains and At1g71030-SRDX, At1g56650-SRDX, and ΔCHS strains were photographed and the images were converted into digital data. Image processing software (Adobe Photoshop) was applied to the resulting digital data to quantify the RGB values in the seed regions. Subsequently, the integrated value of the quantified R, G, and B values was determined. In addition, the ratio relative to the integrated value of the quantified R, G, and B values of wild-type strains was determined. The results are shown in Table 1 and in FIG. 3.

TABLE 1

| Photography lot | Strain | Average | | | Sample standard deviation | | | R × G × B | Increase in R × G × B value relative to WT |
|---|---|---|---|---|---|---|---|---|---|
| | | R | G | B | R | G | B | | |
| 1 | WT (Col-o) | 129.7 | 82.9 | 48.9 | 13.5 | 13.7 | 16.1 | 525,060 | 1.00 |
| | at1g71030-SRDX | 170.1 | 132.8 | 66.9 | 13.2 | 17.5 | 22.8 | 1,510,321 | 2.88 |
| | at1g56650-SRDX | 172.1 | 133.9 | 69.2 | 13.0 | 13.3 | 19.0 | 1,594,257 | 3.04 |
| | Δ CHS | 177.8 | 139.9 | 64.2 | 16.1 | 16.2 | 18.0 | 1,595,139 | 3.04 |
| 2 | WT (Col-o) | 159.1 | 84.8 | 59.8 | 14.3 | 12.1 | 14.7 | 806,880 | 1.00 |
| | at1g56650-SRDX | 197.9 | 182.4 | 126.5 | 12.3 | 12.7 | 13.2 | 4,564,621 | 5.66 |
| 3 | WT (Col-o) | 154.9 | 96.8 | 40.1 | 48.2 | 37.3 | 16.0 | 600,644 | 1.00 |
| | at1g56650-SRDX | 166.4 | 156.1 | 104.6 | 28.3 | 33.0 | 51.4 | 2,717,975 | 4.53 |

Figure 3:
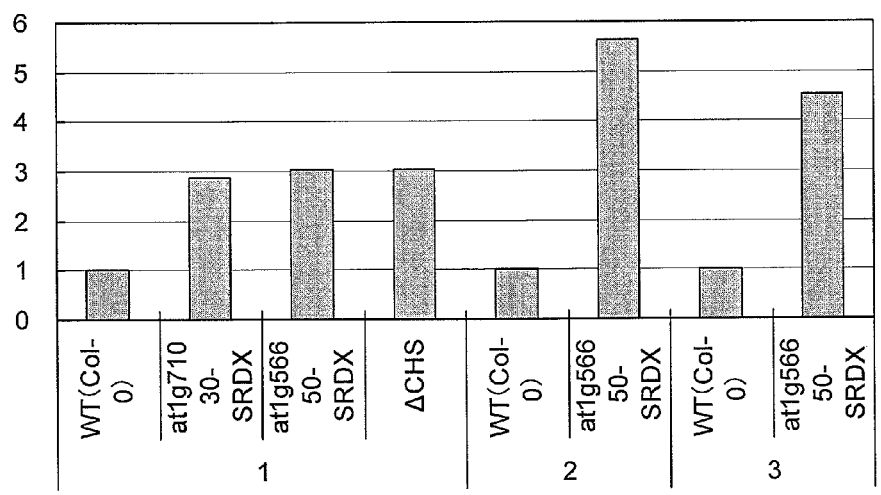
FIG. 3 is a characteristic diagram showing the results of comparing the integrated value of R, G, and B values of seed-coat color determined with the use of image data with that of seeds of wild-type strains.

As shown in Table 1 and FIG. 3, the integrated value of the R, G, and B values of the At1g71030-SRDX strain, the At1g56650-SRDX strain, and the ACHS strain was at least 2.88 times higher than that of wild-type strains. Thus, seed-coat color can be quantitatively assayed with the use of image data of seeds, and the fat-and-oil content in seeds can be evaluated in a very simple and rapid manner.

All publications, patents, and patent applications cited herein are incorporated herein by reference in their entirety.

The invention claimed is:

1. A plant which expresses a chimeric protein, said chimeric protein comprising a transcription factor fused to a repressor domain sequence that converts said transcription factor into a transcription repressor,
wherein said transcription factor is a protein comprising the amino acid sequence of SEQ ID NO: 4,
wherein the repressor domain sequence comprises an amino acid sequence selected from the group consisting of (1) to (8):

(1) X1-Leu-Asp-Leu-X2-Leu-X3      (SEQ ID NO: 21)

wherein X1 represents 0 to 10 amino acid residues; X2 represents Asn or Glu; and X3 represents at least 6 amino acid residues;

(2) Y1-Phe-Asp-Leu-Asn-Y2-Y3      (SEQ ID NO: 22)

wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3      (SEQ ID NO: 23)

wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu      (SEQ ID NO: 24)

wherein Z4 represents Glu, Gln, or Asp;

(5) α1-Leu-β1-Leu-γ1-Leu;      (SEQ ID NO: 25)

(6) α1-Leu-β1-Leu-γ2-Leu;      (SEQ ID NO: 26)

(7) α1-Leu-β2-Leu-Arg-Leu;      (SEQ ID NO: 27)
and (8) α2-Leu-β1-Leu-Arg-Leu      (SEQ ID NO: 28)

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp, and wherein the seeds of said plant exhibit an increase in fat and oil content in comparison to a wild-type plant not expressing said chimeric protein.

2. A method for isolating fat and oil from a plant, comprising separating and recovering fat and oil from the seeds of the plant according to claim 1.

* * * * *